US008303588B2

(12) United States Patent
Nakamura et al.

(10) Patent No.: US 8,303,588 B2
(45) Date of Patent: Nov. 6, 2012

(54) EXTERNAL SKELETAL FIXATION DEVICE

(75) Inventors: Kozo Nakamura, Tokyo-To (JP); Isao Ohnishi, Tokyo-To (JP); Masahiko Bessho, Tsu (JP); Satoru Oohashi, Gifu (JP); Tsuneo Aoki, Niigata (JP); Mitsuo Sato, Agano (JP); Tatsuko Sato, legal representative, Agano (JP); Ryojiro Asano, Sanjo (JP); Kazuo Watanabe, Tokyo-To (JP); Hiroshi Matsuzawa, Tokyo-To (JP); Toshiro Uehara, Tokyo-To (JP); Yoshiharu Saito, Tokyo-To (JP)

(73) Assignees: Kozo Nakamura, Tokyo (JP); Isao Ohnishi, Tokyo (JP); Sunmedix Co., Ltd., Tokyo (JP); Mizuho Ika Kogyo Kabushiki Kaisha, Tokyo (JP)

( * ) Notice: Subject to any disclaimer, the term of this patent is extended or adjusted under 35 U.S.C. 154(b) by 766 days.

(21) Appl. No.: 11/885,484

(22) PCT Filed: Mar. 3, 2005

(86) PCT No.: PCT/JP2005/003608
§ 371 (c)(1),
(2), (4) Date: Oct. 3, 2008

(87) PCT Pub. No.: WO2006/092863
PCT Pub. Date: Sep. 8, 2006

(65) Prior Publication Data
US 2009/0024128 A1   Jan. 22, 2009

(51) Int. Cl.
*A61F 5/04* (2006.01)

(52) U.S. Cl. .................................................. 606/59

(58) Field of Classification Search ............ 606/54, 606/55, 56, 57, 58, 59, 60; 248/231.71, 231.51
See application file for complete search history.

(56) References Cited

U.S. PATENT DOCUMENTS

| | | | | |
|---|---|---|---|---|
| 4,488,542 | A | * | 12/1984 | Helland ........................... 606/59 |
| 5,662,648 | A | * | 9/1997 | Faccioli et al. ................. 606/54 |
| 5,897,555 | A | | 4/1999 | Clyburn et al. |
| 5,944,719 | A | | 8/1999 | Leban |
| 6,019,769 | A | * | 2/2000 | McCarthy et al. ............ 606/105 |
| 6,162,223 | A | * | 12/2000 | Orsak et al. ..................... 606/59 |
| 6,277,118 | B1 | * | 8/2001 | Grant et al. ..................... 606/54 |

(Continued)

FOREIGN PATENT DOCUMENTS
DE    101 25 742 C1    7/2002
(Continued)

*Primary Examiner* — Alvin Stewart
*Assistant Examiner* — Atiya Mahmud
(74) *Attorney, Agent, or Firm* — Birch, Stewart, Kolasch & Birch, LLP

(57) ABSTRACT

An external skeletal fixation device includes first and second pin clamp units fixedly holding rodlike members inserted, respectively, into a first part and a second part of a bone on the opposite sides, respectively, of a virtual hinge point corresponding to a center of rotational angulation, a center on opposite sides of a fracture site of the bone or a part of the osteotomy site for deformity correction are turned, or a center about which a joint turns. A connecting mechanism connecting the first and second pin clamp units has first and second arms pivotally connected to the first and second pin clamp units, respectively. The respective axes of rotary joints respectively connecting the first pin clamp unit and the first arm, the second pin clamp unit and the second arm, and the first arm and the second arms extend toward the virtual hinge point.

14 Claims, 17 Drawing Sheets

U.S. PATENT DOCUMENTS 6,652,524 B1 * 11/2003 Weiner .................. 606/59
2004/0133199 A1 7/2004 Coati et al.

FOREIGN PATENT DOCUMENTS

| | | |
|---|---|---|
| EP | 0704192 A1 | 4/1996 |
| EP | 1 021 992 A2 | 7/2000 |
| FR | 2749499 A1 | 12/1997 |
| JP | 8-507460 A | 8/1996 |
| JP | 2001-524859 A | 12/2001 |
| JP | 2004-523310 A | 8/2004 |
| WO | WO-94/21187 A1 | 9/1994 |
| WO | WO-98/51227 A1 | 11/1998 |
| WO | WO-02/069816 A1 | 9/2002 |
| WO | WO-2004-010893 A2 | 2/2004 |

* cited by examiner

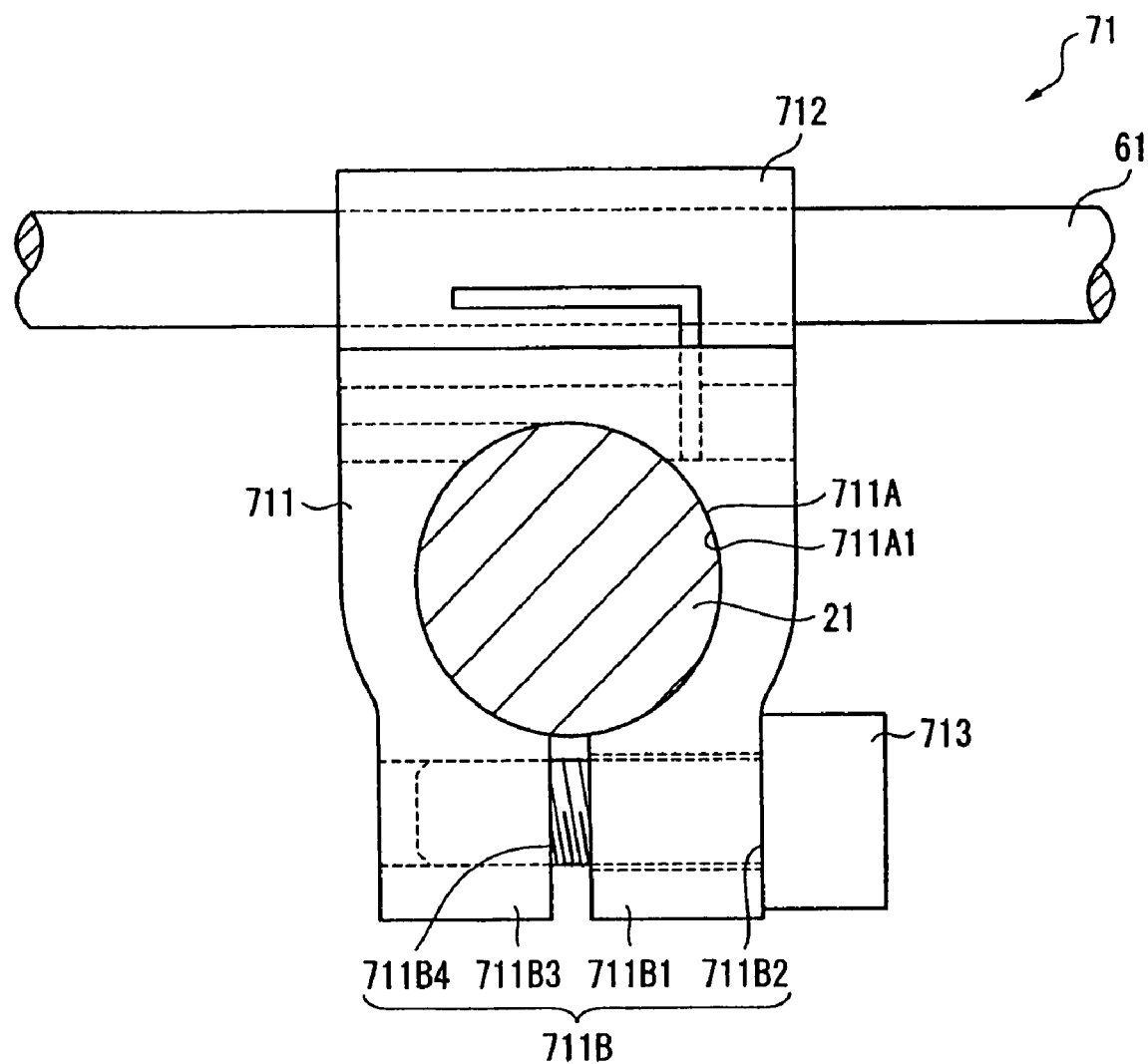
F I G. 7

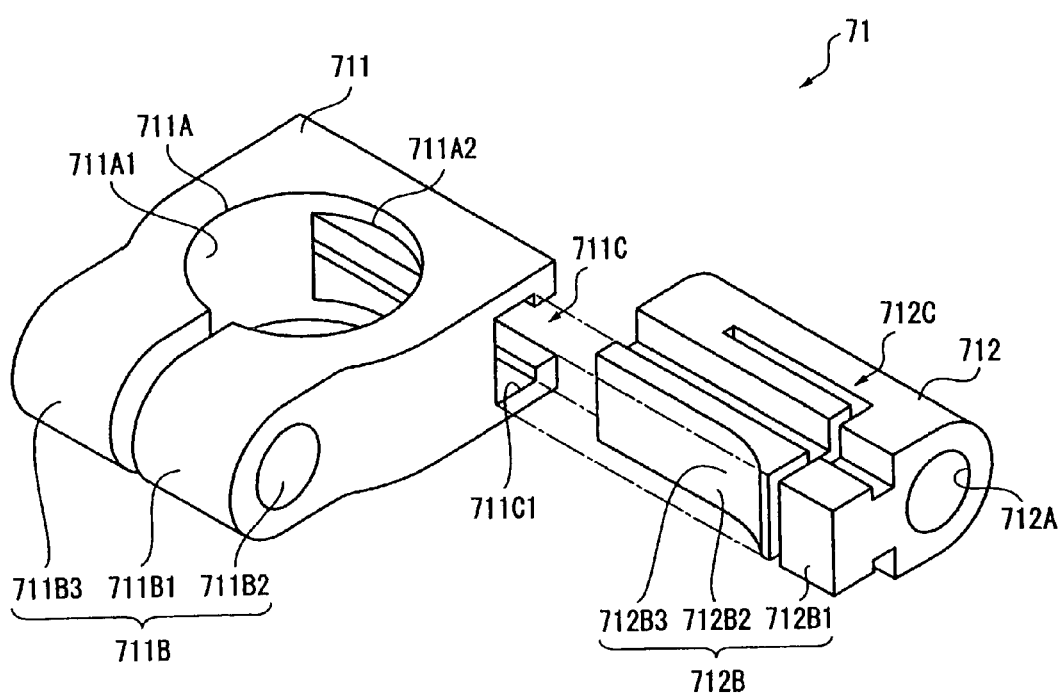
F I G. 8

EXTERNAL SKELETAL FIXATION DEVICE

TECHNICAL FIELD

The present invention relates to an external skeletal fixation device including a pair of clamp members for fixedly holding rodlike members inserted into a first and a second part on the opposite sides of a virtual hinge point in a bone determined at least by the center of rotational angulation of the bone, a center about which a pair of bone fragments on the opposite sides of a fracture site of the bone or an osteotomy site of the bone cut for bone deformity correction are turned or a center of turning of a joint, and a connecting mechanism for connecting the pair of clamp members.

BACKGROUND ART

A known external skeletal fixation device is used for fixing a fractured bone or for bone deformity correction.

The external skeletal fixation device includes plural rodlike members to be inserted into a bone to be fixed from outside the human body, and clamp members for fixedly holding the rodlike members. An Ilizarov external skeletal fixation device disclosed in, for example, Reference document 1, is a known external skeletal fixation device for bone deformity correction. This known external skeletal fixation device includes plural wires as rodlike members to be inserted into a bone, plural ring frames for holding the wires, and a stretchable connecting mechanism for connecting the clamp members. The external skeletal fixation device is disposed so as to surround a deformity point determined as the center of deformation correction.

The Ilizarov external skeletal fixation device fixes the bone with pins held by the clamp members, distracts or shortens the connecting mechanism and corrects the deformation of the bone at the deformity point by extending or twisting the bone in a direction to correct the deformation.

An external skeletal fixation device, such as disclosed in Patent document 1 for holding bones connected by a joint to reduce load on the joint inserts plural half pins, namely, rodlike members, into the radius and the metacarpus and fixes the wrist.

FIG. 17 shows a known external skeletal fixation device 12

Component members of the external skeletal fixation device 12 are made of a metal.

As shown in FIG. 17, the external skeletal fixation device 12 includes a radius traction member 12A for holding half pins 12A1 inserted into the radius 94A, a metacarpus traction member 12B for holding half pins 12B1 inserted into the metacarpus, and a central block 12C connecting the radius traction member 12a and the metacarpus traction member 12B. The half pins 12A1 and 12B1 are attached to the radius traction member 12A and the metacarpus traction member 12B so as to extend perpendicularly to the respective axes of the radius traction member 12A and the metacarpus traction member 12B, respectively. The half pins 12A1 and 12B1 can slide along the radius traction member 12a and the metacarpus traction member 12B, respectively.

The central block 12C of the external skeletal fixation device 12 holds the radius traction member 12A and the metacarpus traction member 12B so as to be turnable relative to each other. The central block 12C permits the following motions (1) to (3) when the hand is in palm down position.

(1) Bending/stretching motions (turning motions about an axis X of turning) on the joint of the central block 12C and the metacarpus traction member 12B according to the vertical movement of the wrist (2) Displacement (turning motions about an axis Y or turning) of the radius 94A/the ulna 94B according to lateral motions of the wrist (3) Pronation/supination (turning motions about an axis Z of turning) on the joint of the radius traction member 12A and the central block 12C according to twisting motions of the wrist Reference document 1: G. A. Ilizarov, "Transosseous Osteosynthesis: Theoretical and Clinical Aspect of the Regeneration and Growth of Tissue" Springer-Verlag, 1992
Patent document 1: JP 2001-524859 A (FIG. 2)

DISCLOSURE OF THE INVENTION

Problem to be Solved by the Invention

The Ilizarov external skeletal fixation device mentioned in Reference document 1 can achieve the deformity correction of a severely deformed bone by using various members in combination. However, it is a first problem in the Ilizarov external skeletal fixation device that the Ilizarov external skeletal fixation device is heavy and bulky, the Ilizarov external skeletal fixation device disposed so as to surround a deformed part including the deformity point cause troubles in daily activities and rehabilitation exercises and exerts great mental and physical loads on the patient equipped with the Ilizarov external skeletal fixation device. A one-sided (monolateral) external skeletal fixation device mentioned in Patent document 1 includes a central block connecting a radius traction member and a metacarpus traction member and provided three individual rotary parts that turn according to the movement of the joint. It is a second problem that clamp members do not move in the direction of movement of the bone, obstruct the movement of the joint and place many restrictions on the movement of the bone and correction direction, and the external skeletal fixation device has a low degree of freedom. It is a third problem that those known external skeletal fixation devices are complicated in construction, requires complicated operations and a long time for mounting the external skeletal fixation device to the bone and requires a skillful surgeon to fix the external skeletal fixation device to the bone.

Since the known external skeletal fixation devices have the first to the third problems, it has been eagerly desired to develop an external skeletal fixation device capable of reducing load on the patient, having a high degree of freedom in the movement and correction direction of a bone during bone deformity correction and rehabilitation exercises, simple in construction and easy to attach to bones.

It is an object of the present invention to provide an external skeletal fixation device capable of reducing load on the patient, allowing the free movement of a bone and bone fragments and bone deformity correction, simple in construction, not requiring a very skillful, experienced surgeon and easy to attach to bones.

Means for Solving the Problem

An external skeletal fixation device according to the present invention includes: a first and a second pin clamp unit for fixedly holding rodlike members inserted into a first and a second part of a bone on the opposite sides, respectively, of a virtual hinge point in the bone corresponding to a center of rotational angulation of the bone, a center on which the first and the second part of the bone respectively on the opposite sides of a fracture site of the bone or an osteotomy site for deformity correction are turned, or a center about which a joint turns; and a connecting mechanism connecting the first and the second pin clamp unit; wherein the connecting mechanism has a first and a second arm pivotally connected to the first and the second pin clamp unit, respectively, the first and the second arms are pivotally joined together, and the respective axes of rotary joints respectively connecting the first arm and the first pin clamp unit, the first and the second arm, and the second arm and the second pin clamp unit extend toward the virtual hinge point.

The virtual hinge point is not a mechanical deformity point in the external skeletal fixation device. The virtual hinge point is a point on which bone fragments supported by the external skeletal fixation device turn and move when the external skeletal fixation device moves.

The external skeletal fixation device according to the present invention including the first and the second pin clamp unit and the connecting mechanism having the first and the second arm is simple in construction.

The first and the second arm of the connecting mechanism are pivotally connected to the first and the second pin clamp unit, respectively, and the axes of the rotary joints on which the first and the second arm turn extend toward the virtual hinge point. Therefore, the external skeletal fixation device can be moved about the virtual hinge point by three-dimensionally turning the first and the second arms. Thus the external skeletal fixation device can be attached to the bone so as to conform to the shape and deformity of the bone and the rodlike members can be surely inserted into and fixed to the bone. One of the bone parts connected to the pin clamp units can be optionally moved relative to the other bone fragment by three-dimensionally moving the first and the second arms about the virtual hinge point. Therefore, the external skeletal fixation device can deal with turning in any correction direction for bone deformity correction. Thus the external skeletal fixation device of the present invention is not only capable of surely fixing the bone, but also capable of increasing the degree of freedom of movement of the bone and correction direction. The external skeletal fixation device can be applied to a wide variety of purposes.

When the conventional external skeletal fixation device is attached to bones so as to transfix a joint with the adjacent bones, the interval between the first and the second pin clamp units does not change when one of the pin clamp units is moved. Since the first and the second pin clamp units holding the rodlike members inserted into the bones do not move in accordance with the movement of the bones, the joint is unable to move freely, the rodlike members inserted into the bones are translated and, in some cases, a burden is imposed on the rodlike members and the patient. In the external skeletal fixation device of the present invention, the respective axes of the rotary joints of the connecting mechanism direct toward the virtual hinge point and the first and the second arm turn relative to each other. Therefore, one of the pin clamp units moves in accordance with the movement of the joint and hence the movement of the joint is not disturbed. Thus the external skeletal fixation device does not hinder the movement of the joint, the breakage of the external skeletal fixation device due to the translation of the rodlike members can be prevented and any burden will not be imposed on the patient.

Since the external skeletal fixation device of the present invention is a monolateral external skeletal fixation device that inserts rodlike members into a bone from one side of the bone, the external skeletal fixation device is simple in construction, the first and the second pin clamp unit can be three-dimensionally arranged by turning the arms, can be easily handled and can be easily attached to and can fix bones. The operator for attaching the external skeletal fixation device to the patient does not need a special skill and experiences. Since the external skeletal fixation device is light as compared with the known Ilizarov external skeletal fixation device, the external skeletal fixation device reduces a physical load on the operator, scarcely disturbs the patient's daily life and rehabilitation exercises and reduces mental load on the patient. Thus, the mental and physical loads on the patient can be effectively reduced.

Preferably, in the external skeletal fixation device according to the present invention, the rotary joints on which the first and the second arm turn relative to the pin clamp units and on which the first and the second arm turn relative to each other include shafts projecting respectively from end part of the first and the second pin clamp unit and one end of the first arm, ring parts formed on the other end of the first arm and opposite ends of the second arm and rotatably put on the shafts respectively, retaining rings put on end parts of the shafts after putting the ring parts on the shafts to press the ring parts against base parts of the shafts, respectively, worm wheels attached to the shafts and provided with teeth arranged around the circumferences thereof, respectively, and worms supported on end parts of the ring parts so as to extend parallel to tangents to the inner circumferences of the ring parts and engaged with the worm wheels, respectively.

Each of the worms is rotated to rotate the worm wheel engaged with the worm, the rotation of the worm wheel is transmitted through the shaft to the pin clamp unit or the arm to turn the arm on the rotary joint relative to the pin clamp unit or the other arm. Therefore, an angle through which the arm turns on the rotary joint can be adjusted by adjusting the rotation of the worm. Since the arm can be turned on the rotary joint after the external skeletal fixation device has been fixedly connected to the bone parts, a displaced bone, a deformed bone and a twisted bone can be corrected and repositioned According to the present invention, it is preferable that each of the first and the second arm has a middle part bent through an angle of approximately 40°.

According to the present invention, the external skeletal fixation device can be fixed to a bone such that the axis of rotation of the rotary part passes the virtual hinge point because the arms are bent through an angle of approximately 40°. The axis of rotation of the rotary part can remain passing the virtual hinge point even if the arms are turned. The effect of directing the rotary part toward the virtual hinge point is always effective.

In the external skeletal fixation device according to the present invention, it is preferable that the component members are made of metal.

The metal may be titanium or duralumin.

According to the present invention, the component members of the external skeletal fixation device are made of a metal. Therefore, the external skeletal fixation device attached to the patient and exposed outside has a sufficient strength and will not be deformed. When the component members are made of titanium resistant to corrosion, the external skeletal fixation device has longterm stability. When the component members are made of duralumin, the external skeletal fixation device is lightweight.

The external skeletal fixation device of the present invention is characterized not only by abilities to reduce the burden on the patient, to permit the free movement of bones and bone fragments and to achieve the correction of deformed bones, but also by simple construction, not needing a skilled, experienced surgeon and facility in attaching the external skeletal fixation device to the patient.

BRIEF DESCRIPTION OF THE DRAWINGS

FIG. 7 is a plan view of a pin clamp included in the first embodiment;

FIG. 8 is an exploded perspective view of the pin clamp included in the first embodiment;

PREFERRED EMBODIMENTS OF THE PRESENT INVENTION

1. First Embodiment

A first embodiment of the present invention will be described with reference to the accompanying drawings.

(1) Outline

Figure 1:
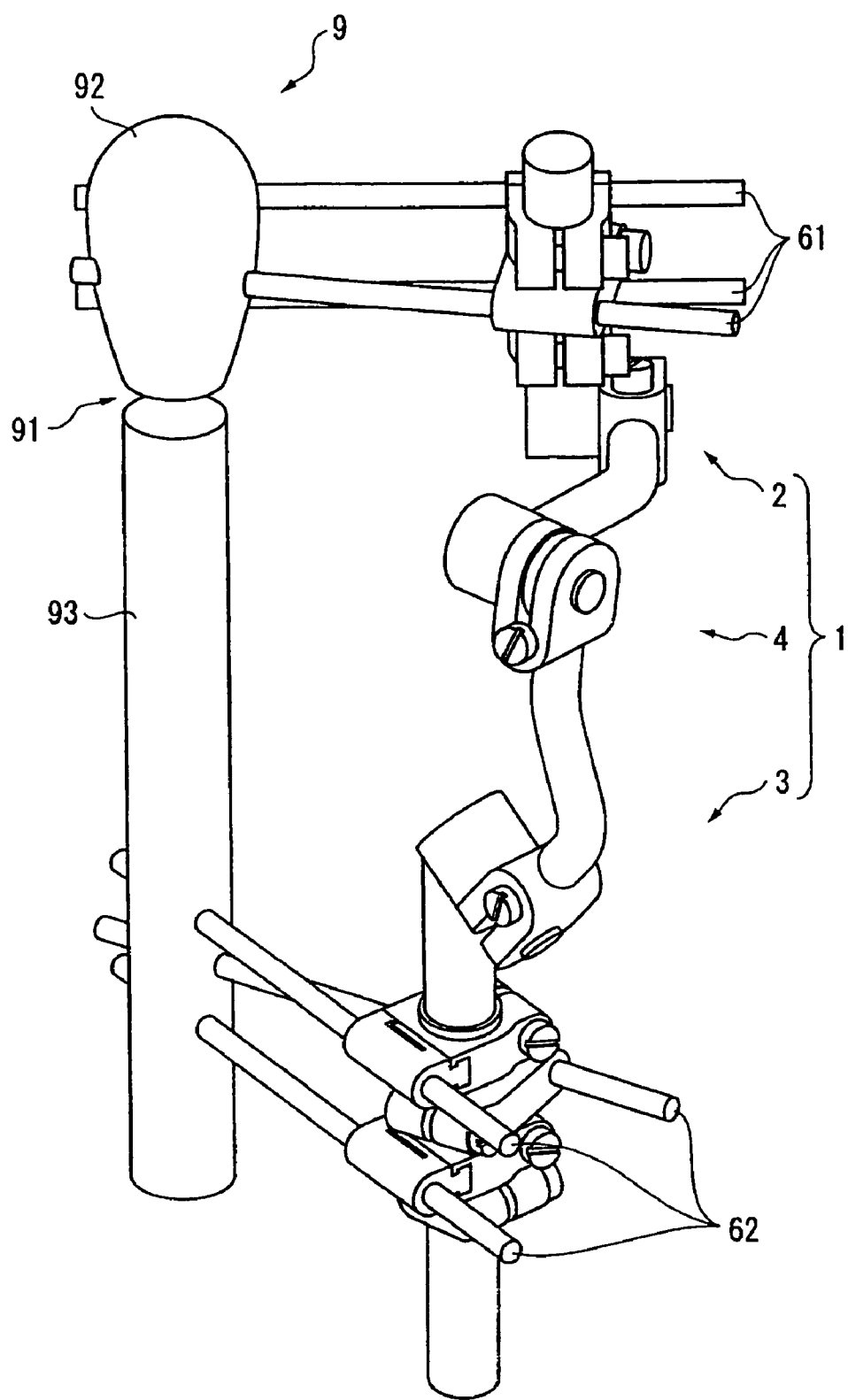
FIG. 1 is a perspective view of an external skeletal fixation device in a first embodiment according to the present invention.

FIG. 1 is a schematic perspective view of an external skeletal fixation device 1 in a first embodiment according to the present invention.

As shown in FIG. 1, the external skeletal fixation device 1 is a fixing device capable of fixedly holding a bone and of optionally correcting a deformed bone. The external skeletal fixation device 1 includes pins 61 and 62, namely, rodlike members, inserted in a bone end 92, namely, a first part, on one side of a virtual hinge point 91 in a bone 9 and a bone shaft 93, namely, a second part, on the other side of the virtual hinge point 91, respectively. A first pin clamp unit 2 and a second pin clamp unit 3, namely, a pair of pin clamp units, fixedly hold the pins 61 and 62, respectively. A connecting mechanism 4 connects the first pin clamp unit 2 and the second pin clamp unit 3 to fix the bone 9. The virtual hinge point 91 is a virtual point determined by at least either of the center of deformation of the bone and a center about which a pair of bone fragments on the opposite sides of a fracture site of the bone or an osteotomy site of the bone for bone deformity correction are turned. In FIG. 1, the virtual hinge point 91 is at a fracture site.

Although the external skeletal fixation device 1 in the first embodiment is supposed to be a device for fixing a single bone, the external skeletal fixation device 1 can be used for fixing two bones connected by a joint. The component members of the external skeletal fixation device 1 are supposed to be made of duralumin. The component members may be made of a metal other than duralumin, such as titanium.

The pins 61 and 62 are metal screw pins. A screw thread, not shown, is formed in free end parts of the pins 61 and 62 to facilitate inserting the pins 61 and 62 into the bone end 92 and the bone shaft 93 and to prevent the pins 61 and 62 from coming off the bone end 92 and the bone shaft 93. The pins 61 have a diameter smaller than that of the pins 62. Metals suitable for forming the pins 61 and 62 are stainless steels and titanium alloy.

(2) Constitution

Figure 2:
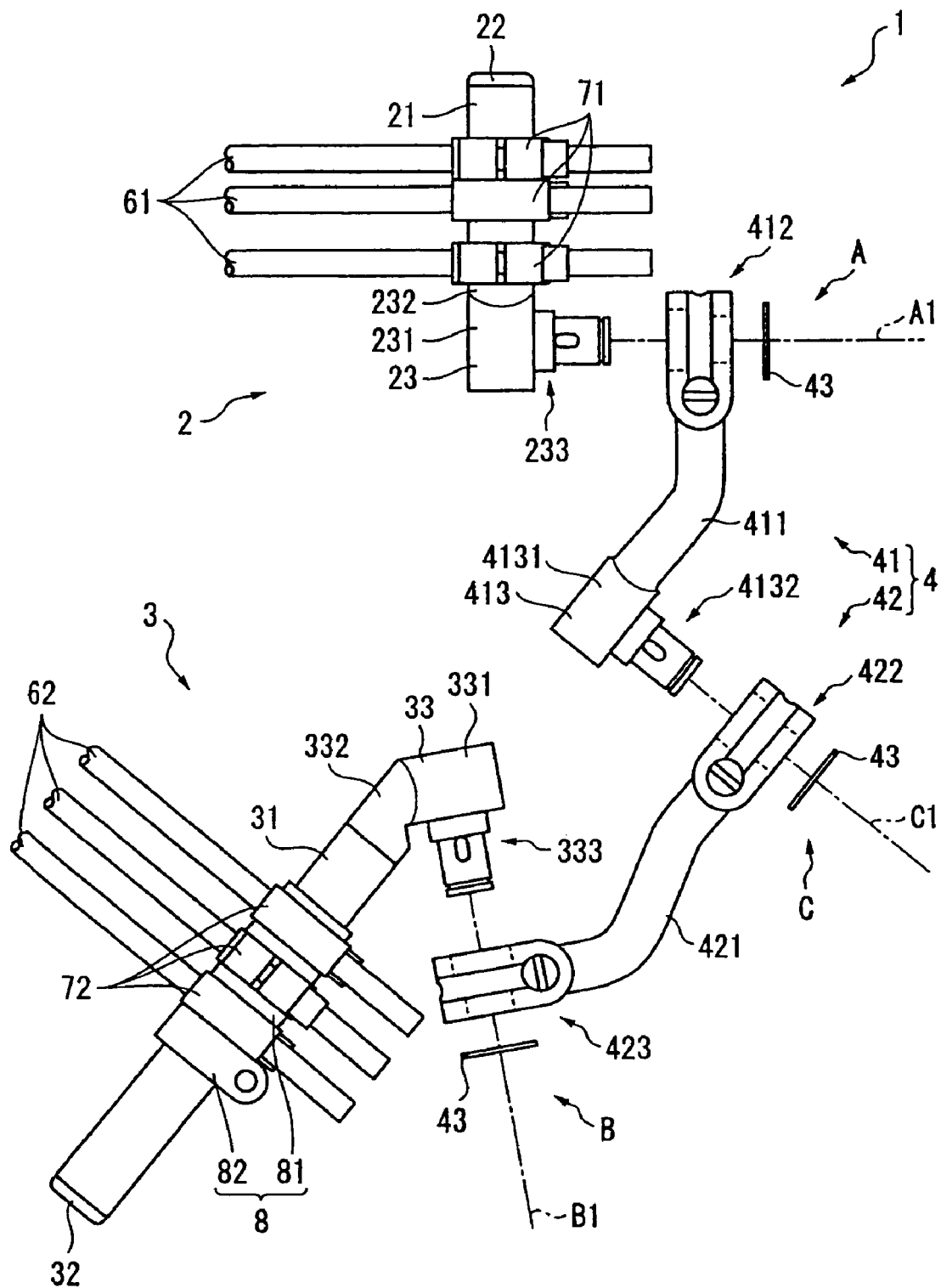
FIG. 2 is an exploded view of the external skeletal fixation device in the first embodiment.

FIG. 2 is an exploded view of the external skeletal fixation device 1.

As shown in FIG. 2, the external skeletal fixation device 1 includes the first pin clamp unit 2 holding the pins 61 inserted into the bone end 92 (FIG. 1), a second pin clamp unit 3 holding the pins 62 inserted into the bone shaft 93 (FIG. 1), and the connecting mechanism 4 provided with a first bar link 41 and a second bar link 42.

(2-1) First Pin Clamp Unit 2

Figure 3:
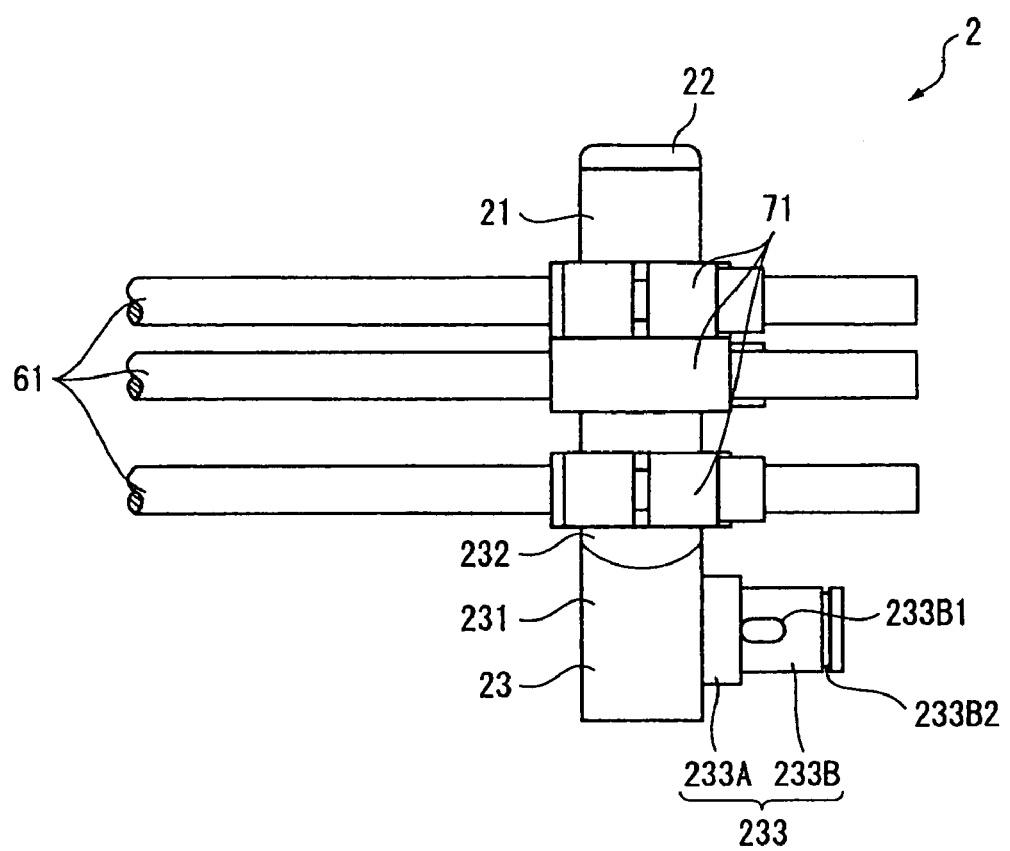
FIG. 3 is a plan view of a first pin clamp unit included in the first embodiment.

FIG. 3 is a plan view of the first pin clamp unit 2.

As shown in FIGS. 2 and 3, the first pin clamp unit 2 includes a pipe 21, a cap attached to one end of the pipe 21, and a rodlike member 23 attached to the other end of the pipe 21.

The pipe 21 is a hollow, cylindrical, metal member disposed substantially parallel to the axis of the bone end 92 (FIG. 1). Pin clamps 71 holding the pins 61 inserted into the bone end 92 are mounted on the pipe 21. Each of the pin clamps 71 holds one of the pins 61. The construction of the pin clamps 71 will be described later.

The rubber cap 22 is attached to the open end of the pipe 21 to close the open end of the pipe 21.

The rodlike member 23 is attached to the end of the pipe 21 opposite the end of the pipe 21 to which the cap 22 is attached. The rodlike member 23 is used for rotatably connecting the pipe 21 to the connecting mechanism 4. The rodlike member 23 has a substantially cylindrical base part 231.

A branch 232 projects from the side surface of the base part 231 perpendicularly to the axis of the base part 231. The branch 232 is a substantially cylindrical part for connecting the rodlike member 23 to the pipe 21. The branch 232 has a substantially cylindrical connecting part in its free end part. The connecting part of the branch 232 has an outside diameter approximately equal to the inside diameter of the pipe 21. The connecting part of the branch 232 is fitted in the pipe 21 to connect the rodlike member 23 to the pipe 21.

A shaft part 233 projects from a substantially circular surface facing a direction opposite an inserting direction in which the pins 61 attached to the pipe 21 are inserted into the bone end 2. The shaft part 233 has the shape of a structure formed by coaxially superposing two cylinders. The shaft part 233 has a large part 233A of a diameter smaller than the outside diameter of the base part 231, and a small part 233B of an outside diameter smaller than that of the large part 233A. An axial key-slot 233B1 is formed in a base part, on the side of the large part 233A, of the small part 233B. A ring groove 233B is formed in a free end part of the small part 233B.

(2-2) Second Pin Clamp Unit 3

Figure 4:
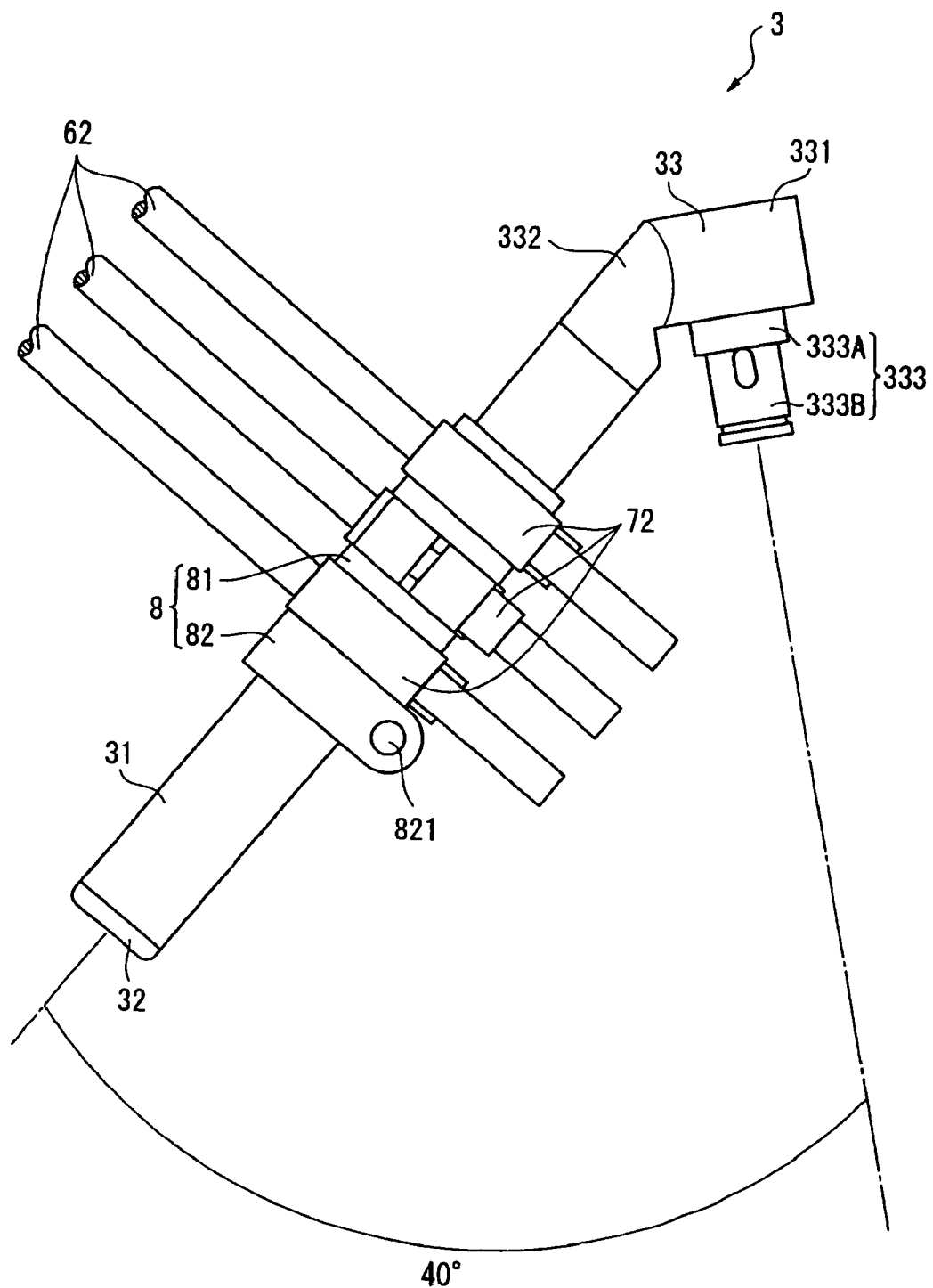
FIG. 4 is a plan view of a second pin clamp unit included in the first embodiment.

FIG. 4 is a plan view of the second pin clamp unit 3.

As shown in FIGS. 2 and 4, the second pin clamp unit 3 is substantially the same in construction as the first pin clamp unit 2 and includes a pipe 31, a cap attached to one end of the pipe 31, and a rodlike member 33 attached to the other end of the pipe 31. The cap 32 is similar to the cap 22 attached to the end of the pipe 21 of the first pin clamp unit 2 and hence the description thereof will be omitted.

The pipe 31 is a hollow, cylindrical, metal member having a length longer than the pipe 21 of the first pin clamp unit 2 and disposed substantially parallel to the axis of the bone shaft 93 (FIG. 1). Pin clamps 72 holding the pins 62 inserted into the bone 93 and a diameter adjusting member 8 are mounted on the pipe 31. The diameter adjusting member 8 is interposed between the pin clamps 72 and the pipe 72.

Each of the pin clamps 72 holds one of the pins 62 on the pipe 31. The pin clamps 72 are substantially the same as the pin clamps 71, except that each of the pin clamps 72 has a part mounted on the pipe 31 greater than that of the pin clamp 71 mounted on the pipe 21 and a pin holding part greater than that of the pin clamp 71 and holding the pin 62 of a diameter greater than that of the pin 61. The pin clamps 72 hold the pins 62 in a matter similar to that in which the pin clamps 71 hold the pins 71 and hence the further description of the pin clamps 72 will be omitted.

The diameter adjusting member 8 adjusts the outside diameter of the pipe 31 to mount the pin clamps 72 closely on the pipe 31. The diameter adjusting member 8 has a substantially cylindrical diameter adjusting part 81 axially slidably put on the pipe 31, and a fastening part 82, for fixedly holding the diameter adjusting member 8 on the pipe 31, formed integrally with the diameter adjusting part 81 at one end of the latter.

The diameter adjusting part 81 is put on the pipe 31 so as to cover the outside surface of the pipe partly with its inside surface in close contact with the outside surface of the pipe 31. The inside diameter of the diameter adjusting part 81 is substantially equal to the outside diameter of the pipe 31. In FIGS. 1, 2 and 4, the number of the pin clamps 72 is three. The three pin clamps 71 are mounted on the diameter adjusting part 81 to hold the pins 72 so as to extend perpendicularly to the axis of the pipe 31.

The fastening part 82 has a substantially U-shaped cross section. The pipe 31 is in contact with the inside surface of the fastening part 82. A threaded hole 821 having an axis perpendicular to the axis of the pipe 31 is formed in an end part of the fastening part 82. A bolt, not shown, is screwed into the threaded hole 821 to fasten the fastening part 82 to the pipe 31. Thus the diameter adjusting member 8 is fixedly mounted on the pipe 31.

The rodlike member 33 is used, similarly to the rodlike member 23 of the first pin clamp unit 2, for rotatably connecting the pipe 31 to the connecting mechanism 4.

The rodlike member 33 has a base part 331 and a branch 332 projecting from the side surface of the base part 331. A shaft part 333 projects from a surface facing a direction opposite an inserting direction in which the pins 62 are inserted into the bone shaft 93.

The base part 331 and the shaft part 333 are substantially similar in shape to the base part 231 and the shaft part 233 of the first pin clamp unit 2, respectively. The shaft part 333 has a large part 333A and a small part 333B of an outside diameter smaller than that of the large part 333A.

The branch 332, similarly to the branch 232 of the rodlike member 23 of the first pin clamp unit 2, is a substantially cylindrical member for connecting rodlike member 33 to the pipe 31. The branch 233 has a substantially cylindrical connecting part similar to that of the branch 232. The connecting part of the branch 332 is fitted in one end of the pipe 31. Whereas the branch 232 is perpendicular to the base part 231, the branch 332 is oblique to the base part 331. The branch 332 projects from the side surface of the base part 331 such that the axis of the branch 332 is inclined at approximately 40° to the axis of the shaft art 333.

(2-3) Connecting Mechanism 4

As shown in FIG. 2, the connecting mechanism 4 is connected to the respective rodlike members 23 and 33 of the first pin clamp unit 2 and the second pin clamp unit 3. The connecting mechanism 4 is provided with the first bar link 41 and the second bar link 42, namely, arms. Base end parts of the bar links 41 and 42 are pivotally joined together.

Figure 5:
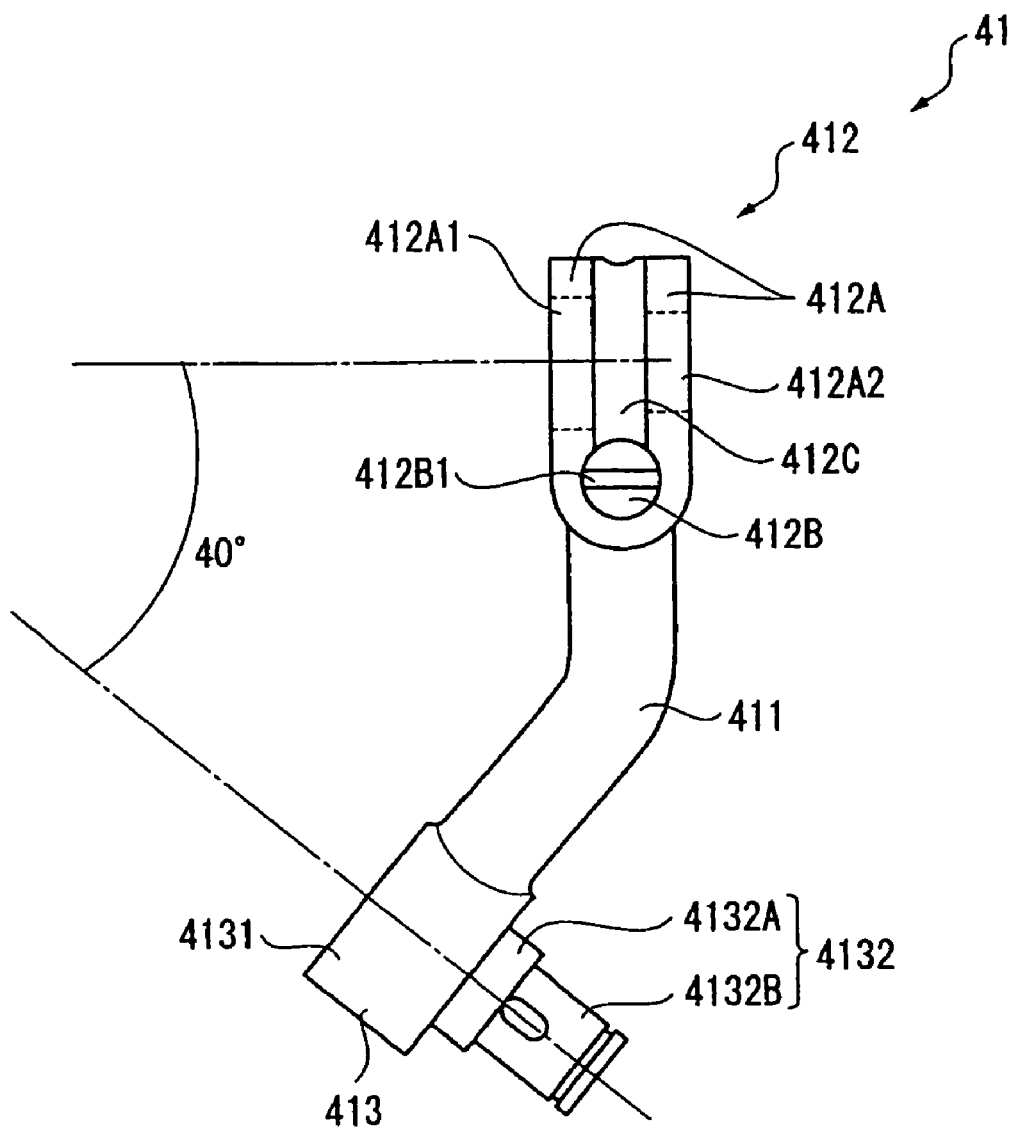
FIG. 5 is a plan view of a first bar link included in the first embodiment.

FIG. 5 is a plan view of the first bar link 41.

As shown in FIGS. 2 and 5, the first bar link 41 made of a metal is put on the rodlike member 23 of the first pin clamp unit 2 so as to be turnable relative to the rodlike member 23. The first bar link 41 has a substantially L-shaped body 411. The body 411 is a hollow, cylindrical member. The body 411 has a first end provided with a first connecting part 412 and a second end provided with a second connecting part 413. The first connecting part 412 is connected to the shaft part 233 of the rodlike member 23.

The first connecting part 412 formed on the first end of the body 411 has a substantially C-shaped cross section. The first connecting part 412 connects the first bar link 41 to the first pin clamp unit 2 so as to be turnable relative to the first pin clamp unit 2. The first connecting part 412 has a pair of ring parts 412A opposed to each other, formed integrally with the body 411 and having the shape of an oval.

The ring parts 412A are provided in their substantially central parts with openings 412A1 and 412A2, respectively. The shaft part 233 of the rodlike member 23 is fitted in the openings 412A1 and 412A2. The body 411 is bent at a small angle. The opening 412A1 formed in one of the ring parts 412A has a diameter equal to that of the large part 233A of the shaft part 233 of the rodlike member 23. The opening 412A2 formed in the other ring part 412A has a diameter substantially equal to that of the small part 233B of the shaft part 233. The first bar link 41 is connected to the shaft part 233 of the first pin clamp unit 2 with a concavely curved surface thereof facing the first connecting unit 2.

A worm 412B, namely, a screw bar, and a worm wheel 412C provided on its circumference with teeth are held between the ring parts 412A. The worm 412B and the worm wheel 412C are engaged.

The worm 412B is disposed in the bottom of a space between the ring parts 412A. A helicoids groove, not shown, is formed in a middle part of the worm 412B. The teeth of the worm wheel 412C are engaged in the helicoids groove of the worm 412B. Grooves 412B1 substantially perpendicular to the axis of the worm 412B are formed respectively in the opposite ends of the worm 412B corresponding to the side surfaces of the ring parts 412A. The worm wheel 412C can be driven for rotation by the worm 412B by rotating the worm 412B with a screwdriver or the like engaged in the groove 412B1.

The worm wheel 412C placed between the ring parts 412A of the first connecting part 412 and is mounted on the shaft part 233 of the rodlike member 23 of the second pin clamp unit 2. The worm wheel 412C is provided on its circumference with the teeth. The worm wheel 412C is provided with a center bore, not shown, and the shaft part 233 is fitted in the center bore of the worm wheel 412C. A keyway is formed in the inside surface of the center bore of the worm wheel 412C at a position corresponding to the key-slot 233B1 formed in the small part 233B (FIG. 3) of the shaft part 233. A key, not shown, is fitted in the keyway and the key-slot 233B1 to interlock the worm wheel 412C and the shaft part 233. A mechanism for rotating the worm wheel 412C and the engagement of the worm wheel 412C and the shaft part 233 will be described later.

The second connecting part 413 formed on the second end of the body 411 is used for pivotally joining the first bar link 41 and the second bar link 42 together. The second connecting part 413 is similar in construction to the rodlike members 23 and 33. The second connecting part 413 has a substantially cylindrical base part 4131 and a shaft part 4132 projecting from the substantially circular end surface of the base part 4131. A part corresponding to the branches 232 and 332 of the rodlike members 23 and 33 extends between the side surface of the base part 4131 and the body 411 and is continuous with the base part 4131 and the body 411. The surface of the base part 4131 from which the shaft part 4132 projects is on the side of a convexly curved surface of the body 411. The shaft part 4132, similarly to the shaft parts 233 and 333 of the rodlike members 23 and 33, has a large part 4132A and a small part 4132B.

The body 411 of the first bar link 41 has the bent middle part and is formed substantially in an L-shape. The body 411 is bent such that an angle between the common axis of the openings 412A1 and 412A2 of the ring parts 412A of the first connecting part 41 and the center axis of the shaft part 4132 of the second connecting part 413 is approximately 40°. The middle part of the first bar link 41 is thus bent so that one part of the first bar link 41 on one side of the bend is inclined at approximately 40° to the other part of the same on the other side of the bend. The opening 412A1 of the first connecting part 412 is on the side of the concave surface of the first bar link 41 and the shaft part 4132 of the second connecting part 413 is on the side of the convex surface of the first bar link 41.

Figure 6:
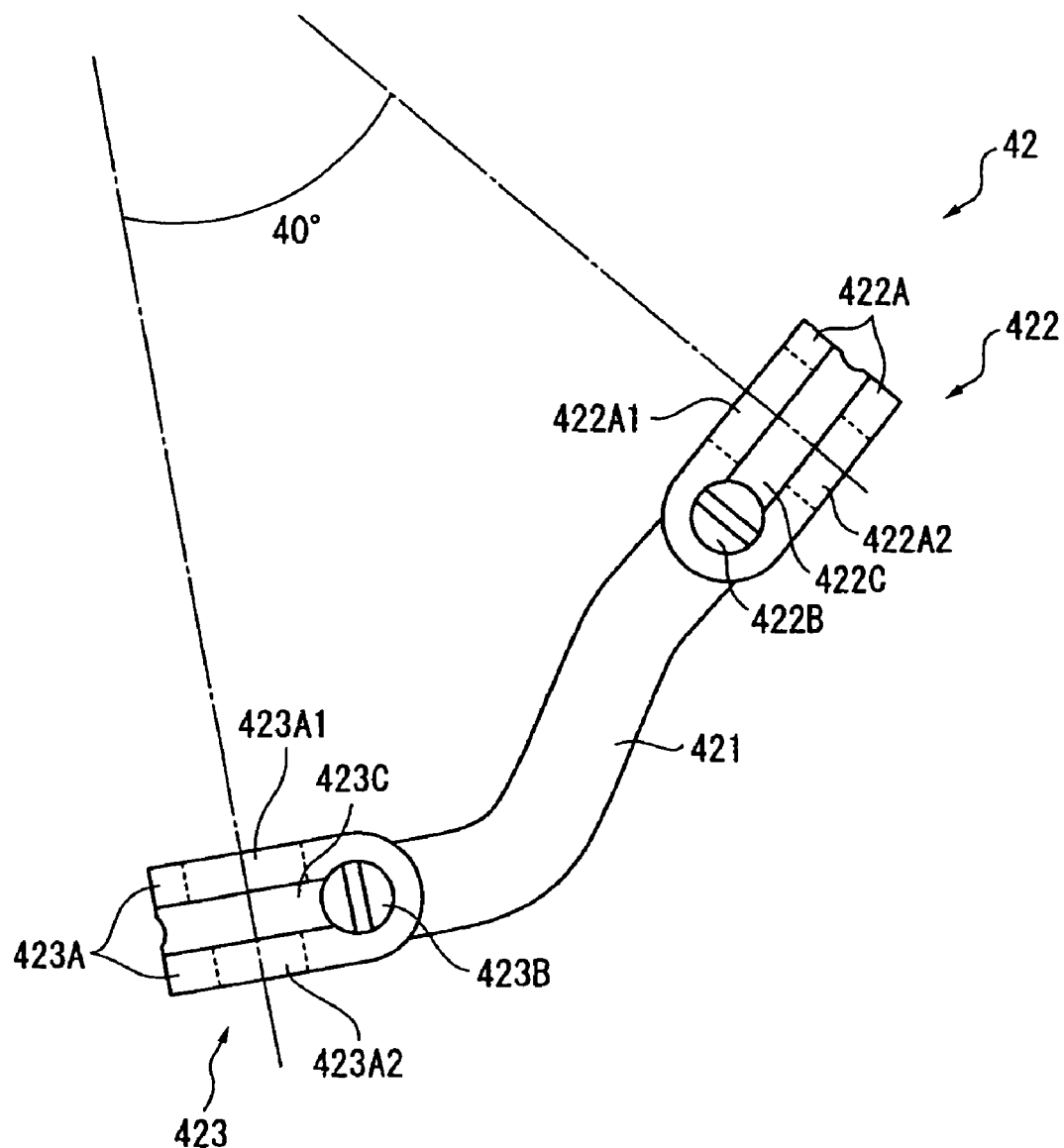
FIG. 6 is a plan view of a second bar link included in the first embodiment.

FIG. 6 is a plan view of the second bar link 42.

As shown in FIGS. 2 and 6, the second bar link 42 has a first end connected to the first bar link 41 and a second end connected to the second connecting unit 3. The second bar link 42 has a bent body 421. The body 421 has one end provided with a first connecting part 422 connected to the second connecting part 413 of the first bar link 41 and the other end provided with a second connecting part 423 connected to the shaft part 333 of the rodlike member 33 of the second pin clamp unit 3.

The body 421 is a substantially S-shaped, hollow, cylindrical member. The first connecting part 422 and the second connecting part 423 formed respectively on the opposite ends of the body 421, similarly to the first connecting part 412 of the first bar link 41, are provided with a pair of ring parts 422A and a pair of ring parts 423A, respectively. The inner ring parts 422A and 423A on the side of the inner curved surface of the body 421 are provided with openings 422A1 and 423A1, respectively. The outer ring parts 422A and 423A on the side of the outer curved surface of the body 421 are provided with openings 422A2 and 423A2, respectively. The respective diameters of the openings 422A1 and 423A1 correspond to the respective diameters of the large part 4132A (FIG. 5) of the shaft part 4132 of the first bar link 41 and the large part 333A (FIG. 4) of the second pin clamp unit 3, respectively. The respective diameters of the openings 422A2 and 423A2 correspond to the respective diameters of the small part 4132B (FIG. 5) of the shaft part 4132 and the small part 333B (FIG. 4) of the shaft part 333, respectively. The first connecting part 422 and the second connecting par 423, similarly to the connecting part 412 of the first bar link 41, hold a combination of a worm 422B and a worm wheel 422C and a combination of a worm 423B and a worm wheel 423C, respectively. The arrangement of the worms 422B and 423B and the worm wheels 422C and 423C in the first connecting part 422 and the second connecting part 423 is the same as that of the worm 412B and the worm wheel 412C in the connecting part 412 and hence the description thereof will be omitted.

Bends in the body 421 will be described.

The first connecting part 422 and the second connecting part 423 are formed on the opposite ends of the body 421, respectively. The angle of intersection between the center axis of the openings 422A1 and 422A2 of the first connecting part 422 and the center axis of the openings 423A1 and 423A2 of the second connecting part 423 is approximately 40°. Thus the body 421 is a member having a bend bent at approximately 40°.

(3) Engagement of the Shaft Part 233 and the Connecting Part 412

A rotary joint A formed by fitting the shaft part 233 of the rodlike member 23 of the first pin clamp unit 2 in the connecting part 412 of the first bar link 41 will be described. A rotary joint B formed by fitting the shaft part 333 of the rodlike member 33 of the second pin clamp unit 3 in the second connecting part 423 of the second bar link 42 and a rotary joint C formed by fitting the shaft part 4132 of the connecting part 413 of the first bar link 41 in the first connecting part 422 of the second bar link 42 are similar in construction to the rotary joint A and hence the description thereof will be omitted. The rotary joints A, B and C rotate about axes A1, B1 and C1 of rotation, respectively.

Referring to FIGS. 2, 3 and 5, in the rotary joint A, the shaft part 233 of the first pin clamp unit 2 is inserted into the ring parts 412A of the first bar link 41 through the large opening 412A1 and the small opening 412A2 in that order. The surface of the base 231 from which the shaft part 233 projects is brought into contact with the outside surface of the ring part 412A provided with the opening 412A1. The diameter of the opening 412A1 corresponds to the diameter of the large part 233A and the diameter of the opening 412A2 of the other ring part 412A corresponds to the diameter of the small part 233B of the shaft part 233. The key is fitted in the keyway, not shown, formed in the inside surface of the center bore of the work wheel 421C and the key-slot 233B1 formed in the small part 233B to interlock the worm wheel 412C and the shaft part 233. Thus the rotation of the worm wheel 412C is transmitted to the small part 233B of the shaft part 233. A retaining ring 43 is fitted in the ring groove 233B2 formed in the small part 233B of the shaft part 233 inserted into the ring parts 412A to restrict the first pin clamp unit 2 from separating from the ring parts 412A. When the worm 412B held between the ring parts 412A is rotated to rotate the worm wheel 412C engaged with the worm 412B, the rotation of the worm wheel 412C is transmitted through the key to the small part 233B of the shaft part 233 to turn the first pin clamp unit 2 and the first bar link 41 relative to each other about the axis A1 of rotation of the rotary joint A.

The turning of the first pin clamp unit 2 and the first bar link 41 relative to each other on the rotary joint A and the rotation of the worm wheel 412C are prevented by screwing a bolt, not shown, into a threaded hole, not shown, formed in the ring part 412A holding the small part 233B of the first pin clamp unit 2.

(4) Construction of the Pin Clamps 71, Fastening the Pin Clamps 71 to the Pipe 21 and Holding the Pins 61 by the Pin Clamps 71

FIG. 7 is a plan view of an assembly of the pin clamp 71, the pipe 21 and the pin 61. FIG. 8 is an exploded perspective view of the pin clamp 71.

Referring to FIGS. 7 and 8, the pin clamp 71 is a device made of metal to hold the pin 61 on the pipe 21. The pin clamp 71 has a gripping member 711 for gripping the pipe 21, a pin clamp member 712 and a fastening bolt 713 for fastening the gripping member 711 to the pipe 21. The pin clamps 72 are similar in construction to the pin clamps 71 and hence the description thereof will be omitted.

The gripping member 711 has a plane shape substantially resembling the letter U. The gripping member 711 is provided in a substantially central part thereof with an opening 711A for receiving the pipe 21, and in a base part with a groove 711C for receiving the pin clamp member 712. The gripping member 711 has a fastening part 711B holding the bolt 713.

The opening 711A is formed in a shape corresponding to the circumference of a cross section of the pipe 21. The side surface 711A1 of the opening 711A comes into close contact with the outer surface of the pipe 21. A substantially rectangular opening 711A2 (FIG. 8) is formed in the side surface 711A1 so as to open into the groove 711C in the base part.

The fastening part 711B has fastening arms 711B1 and 711B3. A space between the fastening arms 711B1 and 711B3 opens into the opening 711A.

The fastening part 711B is formed in a free end part of the gripping member 711. As mentioned above, the fastening part 711B has the opposed fastening arms 711B1 and 711B3. A through hole 711B2 for receiving the bolt 713 (FIG. 7) is formed in the fastening arm 711B1. A threaded hole 711B4 (FIG. 7) is formed coaxially with the through hole 711B2 in the fastening arm 711B3. the bolt 713 is inserted into the through hole 711B2 and is screwed into the threaded hole 711B4.

The groove 711C is formed in the base part of the gripping member 711 so as to extend substantially perpendicularly to the axis of the pipe 21. The groove 711C has an open end 711C1. The pin clamp member 712 is inserted through the open end 711C1 into the groove 711C. A substantially middle part of the groove 711C opens into the opening 711A2 formed in the side surface of the opening 711A.

The pin clamp member 712 holds the pin 61. The pin clamp member 712 is inserted into the groove 711C of the gripping member 711. The pin clamp member 712 is provided with a pin clamp bore 712A for receiving the pin 61, a contact surface, not shown, with which the side surface of the pin 61 inserted into the pin clamp bore 712A comes into contact, and a sliding part 712B fitted in the groove 711C. A cut 712C is formed in the contact surface and the sliding part 712B.

The pin clamp bore 712A is formed substantially longitudinally in the pin clamp member 712.

The sliding part 712B is fitted in the groove 711C of the gripping member 711. The sliding part 712B is divided into a first sliding part 712B1 and a second sliding part 712B2 by the substantially L-shaped cut 712C having a section extending perpendicularly to the axis of the pin 61 and a section extending along the axis of the pin 61. A front part of the second sliding part 712B, with respect to a direction in which the sliding part 712B is inserted into the groove 711C, has a thickness smaller than the depth of the groove 711C. A middle part of the second sliding part 712B is a control part 712B3 having a shape conforming to that of the pipe 21. The first sliding part 712B1 on the back side with respect to the direction in which the sliding part 712B is inserted into the groove 711C has a thickness substantially equal to the depth of the groove 711C. When the pin clamp member 712 is put on the gripping member 711, the middle part, namely, the control part 712B3, having the shape conforming to that of the pipe 21, of the second sliding part 712B2 protrudes through the opening 711A2 formed in the side surface 711A of the opening 711A toward the center of the opening 711A. Since the cut 712C opens in the side surface 711A1, the control part 712B3 can be bent toward the pin 61.

(4-2) Attachment of the pin clamp 71 to the pipe 21 and holding the pin 61 by the pin clamp 71

Figure 9:
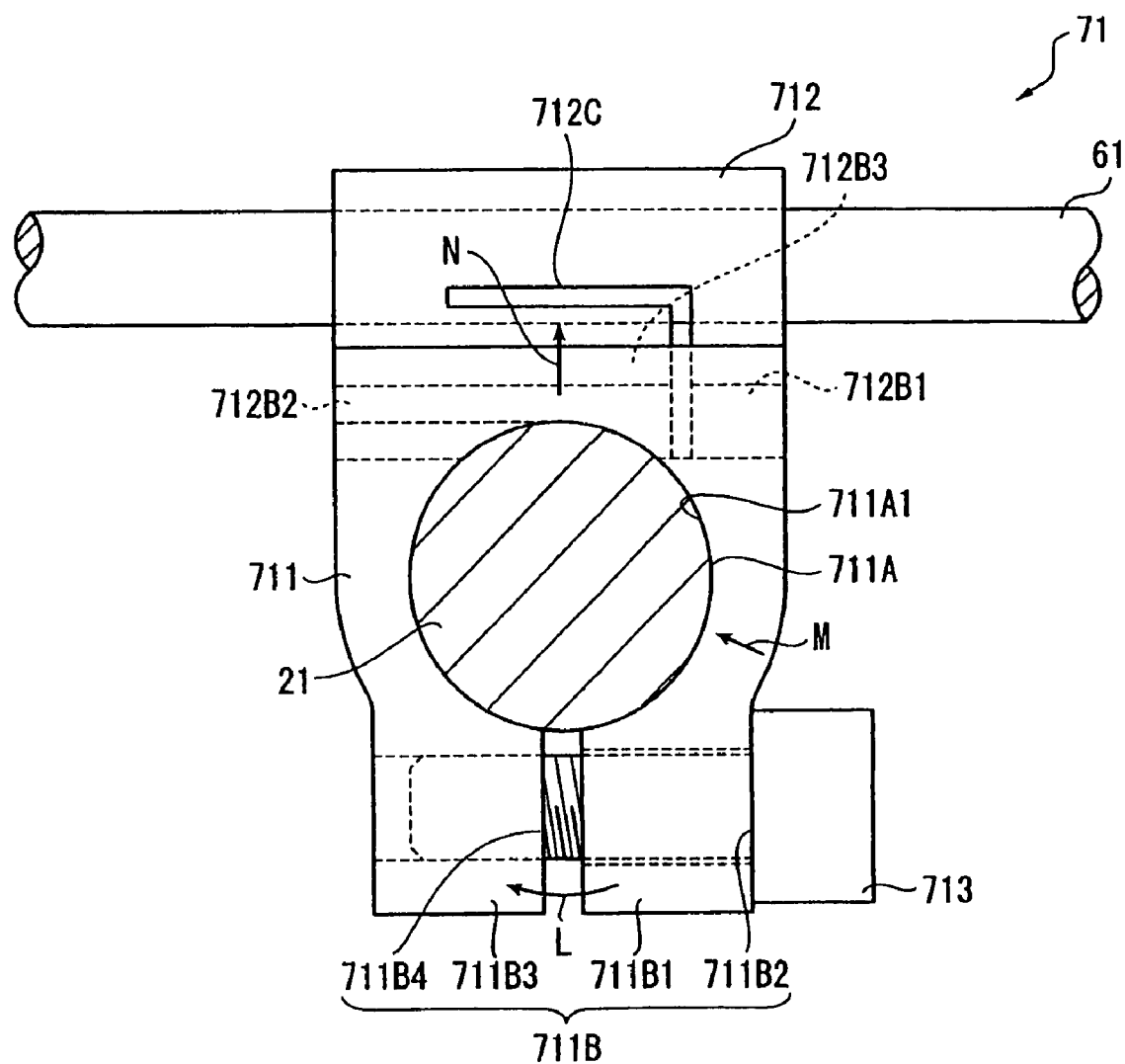
FIG. 9 is a plan view of the pin clamp included in the first embodiment.

FIG. 9 is a plan view of the pin clamp 71 and is a view of assistance in explaining process of attaching the pin clamp 71 to the pipe 21 and holding the pin 61 by the pin clamp 71 by means of the bolt 713.

The process of attaching the pin clamp 71 to the pipe 21 and holding the pin 61 by the pin clamp 71 will be explained with reference to FIG. 9. The manner of holding the pin 62 by the pin clamp 72 and that of attaching the pin clamp 72 through the diameter adjusting member 8 to the pipe 31 are substantially the same as those of holding the pin 61 by the pin clamp 71 and attaching the pin clamp 71 to the pipe 21 and hence the description thereof will be omitted.

The pin 61 is inserted into the pin clamp bore 712A (FIG. 8) of the pin clamp member 712 of the pin clamp 71 so as to bring the side surface of the pin 61 into contact with the contact surface, not shown. The pipe 21 is inserted into the opening 711A formed in the gripping member 711 so as to bring the side surface of the pipe 21 into contact with the side surface 711A1. Then, the bolt 713 is passed through the through hole 711B2 formed in the fastening arm 711B1 of the fastening part 711B and is screwed in the threaded hole 711B4 formed in the fastening arm 711B3 to fasten the gripping member 711 to the pipe 21. As the bolt 713 is screwed into the threaded hole 711B4, the head of the bolt 713 presses the fastening arm 711B1 in the direction of the arrow L. Consequently, the fastening arm 711B1 approaches the other fastening arm 711B3, the diameter of the opening 711A decreases and the side surface 711A1 applies pressure to the pipe 21 radially inward, i.e., in the direction of the arrow M. Thus the pin clamp 71 is fastened to the pipe 21. When the diameter of the opening 711A is thus decreased, the control part 712B3 of the second sliding part 712B protruding through the opening 711A2 (FIG. 8) formed in the side surface 711A1 and in contact with the side surface of the pipe 21 is pressed in the direction of the arrow N. Then, a contact surface of the control part 712B3 in contact with the pin 61 applies pressure diametrically to the pin 61. Consequently, the pin 61 is held firmly between the contact surface of the control part 712B3 and the side surface of the pin clamp bore 712A. Thus the pipe 21 in contact with the side surface 711A1 is gripped by the gripping member 711 and the pin 61 is held between the contact surfaces when the bolt 713 passed through the through hole 711B2 is screwed into the threaded hole 711B4. Thus the pin clamp 71 is fastened to the pipe 21 and holds the pin 61.

When the bolt 713 is unfastened, the pin clamp 71 loosens and releases the pipe 21 and the pin 61.

(5) Linkage Included in the External Skeletal Fixation Device

Figure 10:
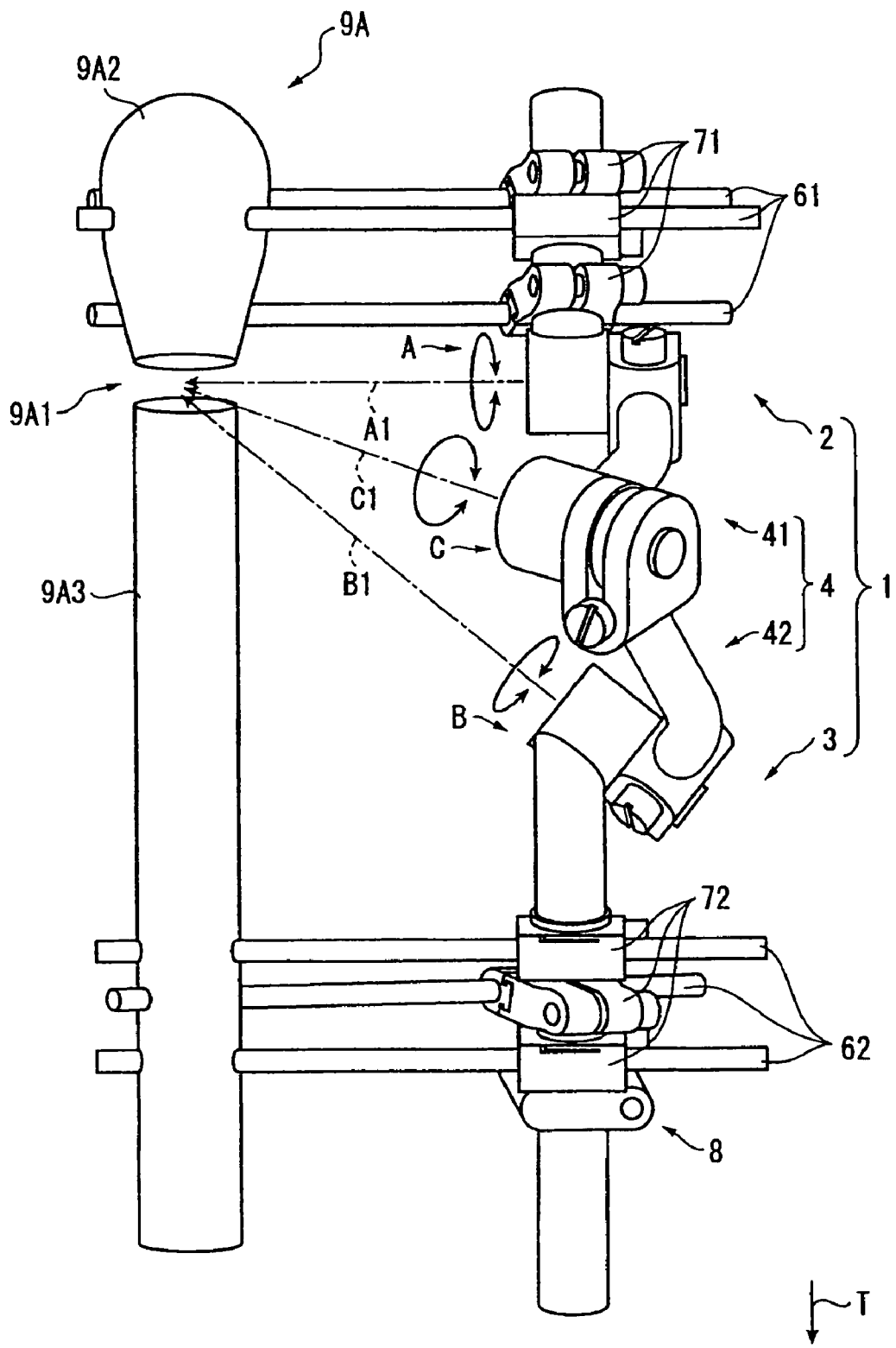
FIG. 10 is a perspective view of assistance in explaining operations of a connecting mechanism included in the external skeletal fixation device in the first embodiment.

FIGS. 10 to 13 are views of assistance in explaining bending motions of the connecting mechanism 4, i.e., motions of a linkage resulting from the turning motions of the rotary joints A, B and C. FIG. 10 shows the external skeletal fixation device 1 attached to a bone end 9A2 and a bone shaft 9A3 of a scarcely curved bone 9A. The bone end 9A2 and the bone shaft 9A3 are not twisted about the axis of the bone 9A. FIG.

Figure 12:
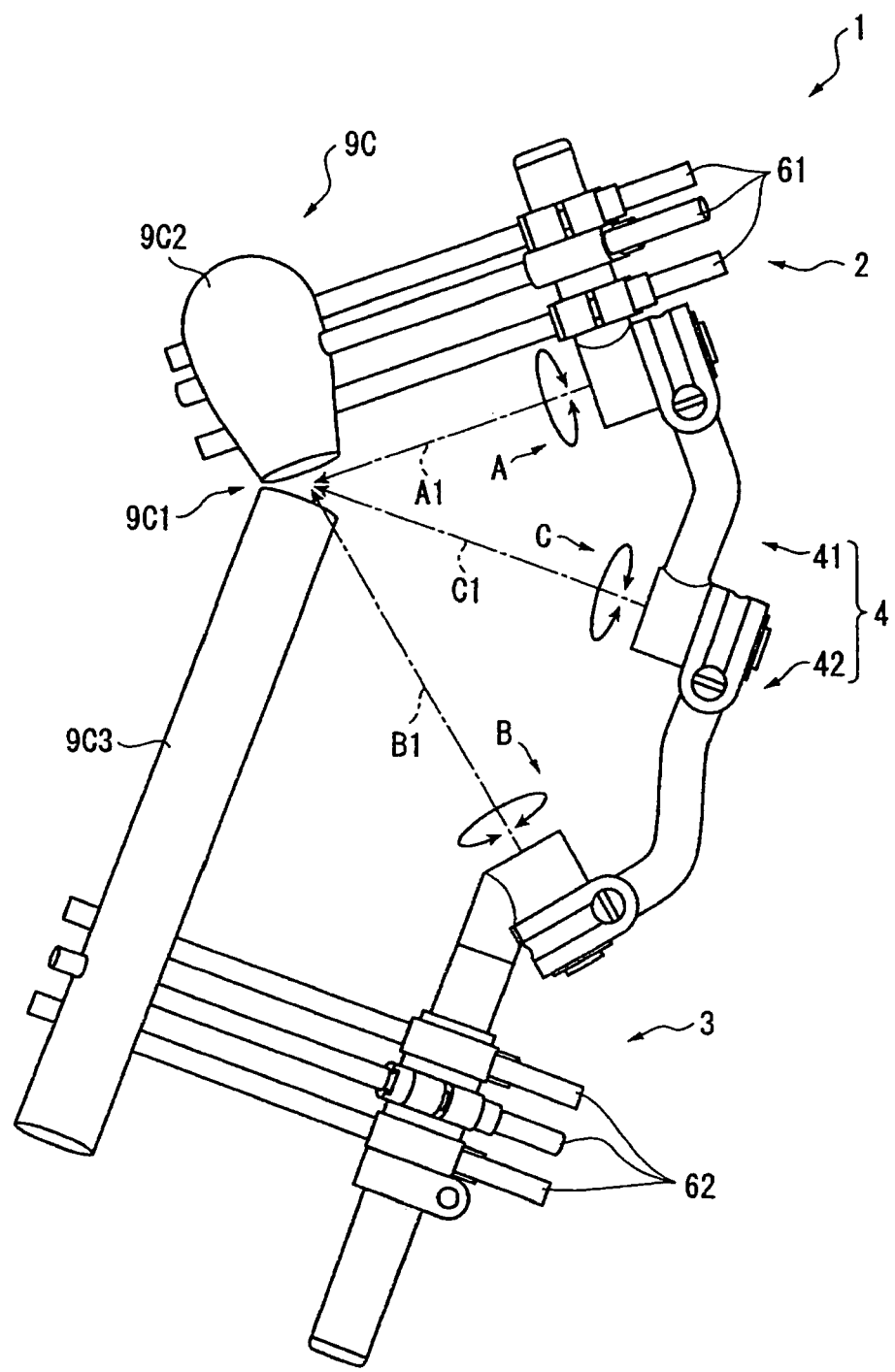
FIG. 12 is a perspective view of assistance in explaining operations of the connecting mechanism included in the external skeletal fixation device in the first embodiment.
Figure 13:
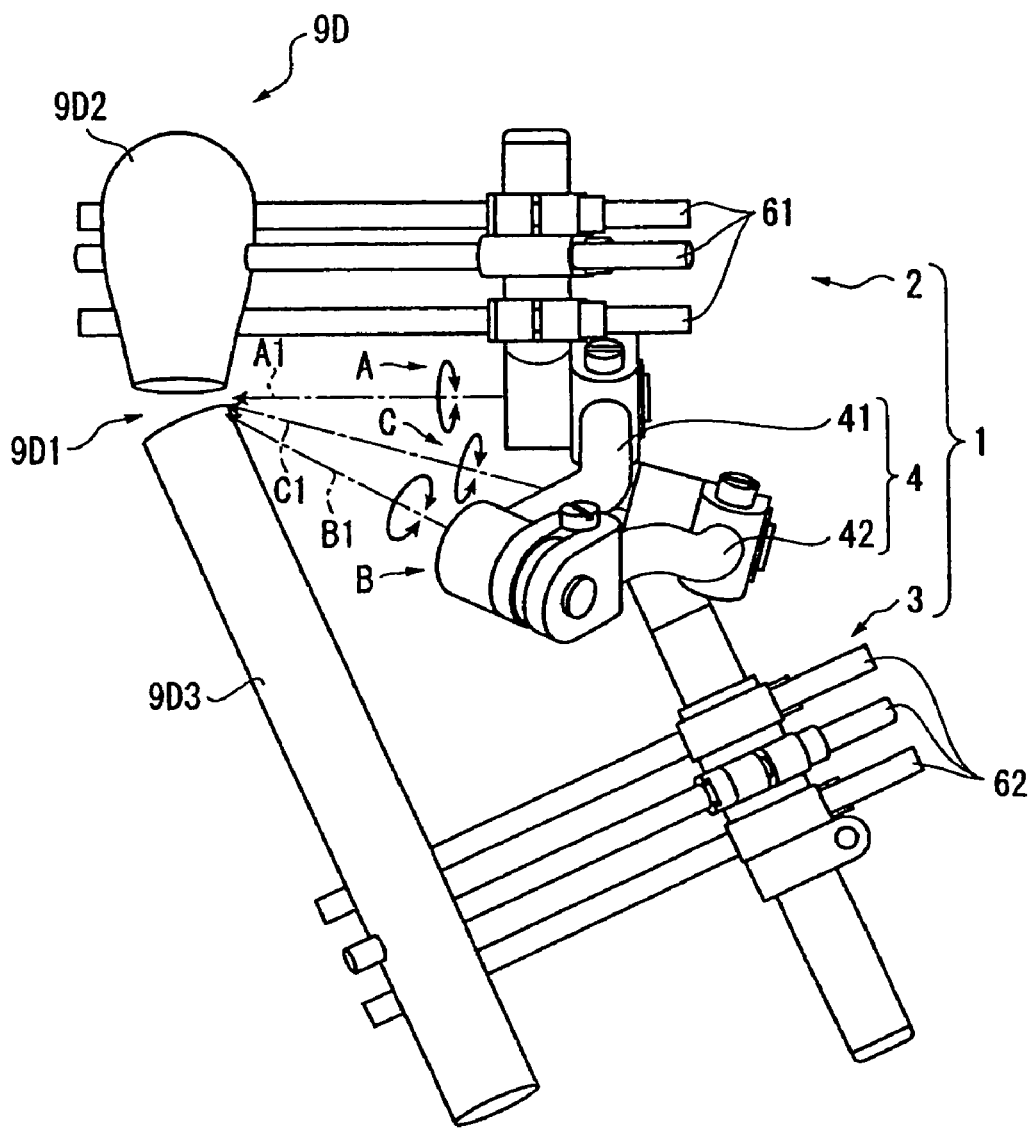
FIG. 13 is a perspective view of assistance in explaining operations of the connecting mechanism included in the external skeletal fixation device in the first embodiment.

11 shows the external skeletal fixation device 1 attached to a bone end 9B2 and a bone shaft 9B3 of a scarcely curved bone 9B. The bone end 9A2 and the bone shaft 9A3 are twisted about the axis of the bone 9B. FIG. 12 shows the external skeletal fixation device 1 attached to a curved bone 9C from the convex side of the bone 9C. FIG. 13 shows the external skeletal fixation device 1 attached to a curved bone 9D from the concave side of the bone 9D.

In the external skeletal fixation device 1, the first pin clamp unit 2 and the first bar link 41, the second pin clamp unit 3 and the second bar link 42, and the first bar link 41 and the second bar link 42 can turn relative to each other on the rotary joints A, B and C, respectively. Thus the external skeletal fixation device 1 can is allowed to move in a three-dimensional space. As shown in FIGS. 10 to 13, the external skeletal fixation device 1 the first pin clamp unit 2 and the second pin clamp unit 3 can be three-dimensionally disposed relative to the bone by turning the first bar link 41 and the second bar link 42 on the joints A, B and C. On the other hand, the bone end 9A2 and the bone shaft 9A3, the bone end 9B2 and the bone shaft 9B3, and the bone end 9C2 and the bone shaft 9C3 can be moved relative to each other by turning the first bar link 41 and the second bar link 42 on the joints A, B and C.

The linkage of the external skeletal fixation device 1 will be described with reference to FIGS. 10 to 13.

Referring to FIG. 10, the bone 9A connected to the external skeletal fixation device 1 is scarcely curved. A bone end 9A2 and a bone shaft 9A3 on the opposite sides, respectively, of a virtual hinge point 9A1 are not twisted about the bone axis. The first pin clamp unit 2 and the second pin clamp unit 3 are in one and the same plane when the external skeletal fixation device 1 is attached to the bone 9A. The pins 61 and 62 held by the external skeletal fixation device 1 are inserted into the bone end 9A2 and the bone shaft 9A3, respectively, from the same direction and are substantially parallel to each other. When the external skeletal fixation device 1 is thus attached to the bone 9A, axes A1, B1 and C1 about which the first bar link 41 and the second bar link 42 of the connecting mechanism 4 turn intersect each other at the virtual hinge point 9A1.

Figure 11:
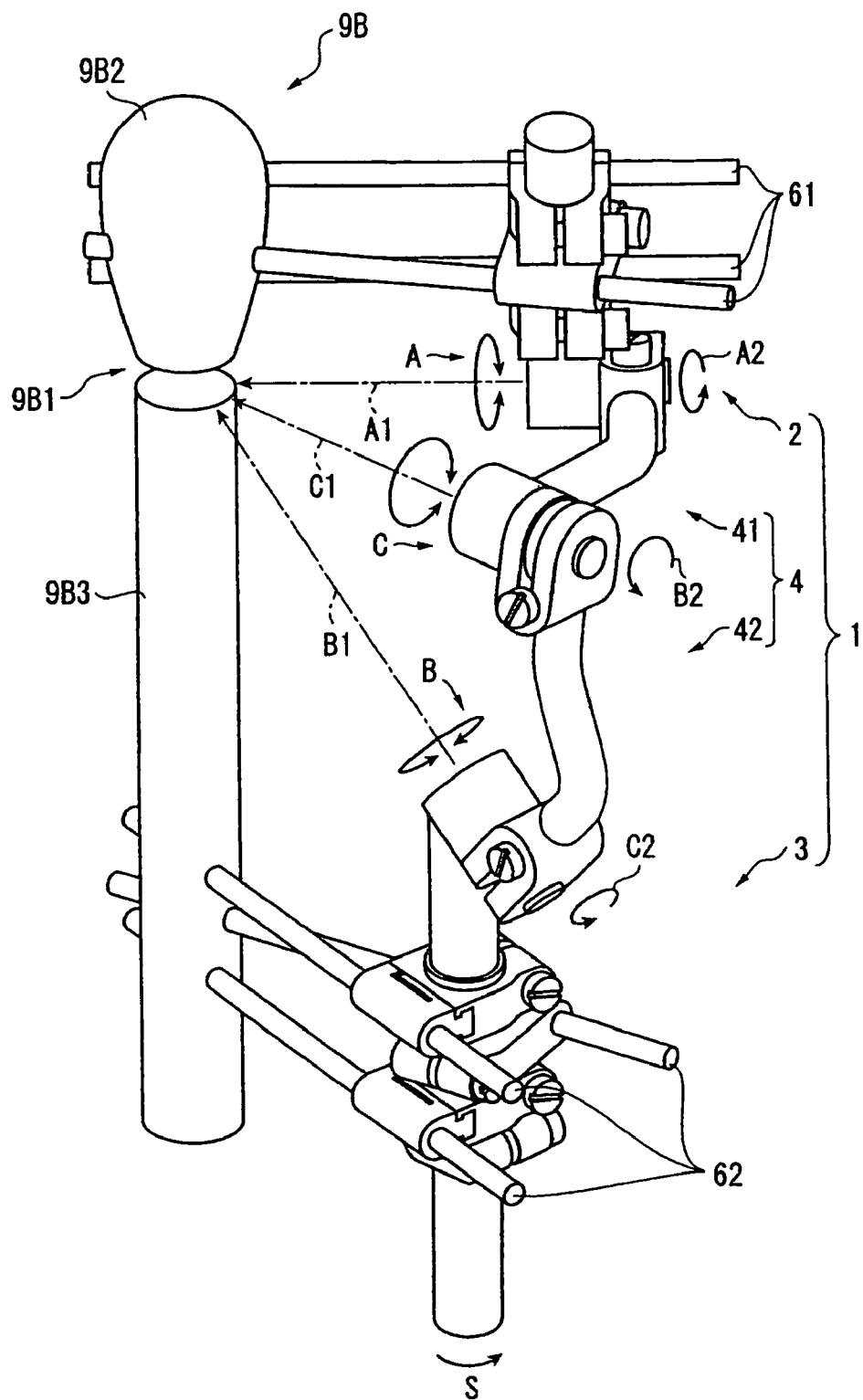
FIG. 11 is a perspective view of assistance in explaining operations of a connecting mechanism included in the external skeletal fixation device in the first embodiment.

Referring to FIG. 11, the bone 9B connected to the external skeletal fixation device 1 is scarcely curved. A bone end 9B2 and a bone shaft 9B3 on the opposite sides, respectively, of a virtual hinge point 9B1 are twisted about the bone axis. The first pin clamp unit 2 and the second pin clamp unit 3 are in different planes, respectively, because the first bar link 41 and the second bar link 42 of the connecting mechanism 4 are turned about the axes A, B and C to dispose the first pin clamp unit 2 and the second pin clamp unit 3 so as to conform to the twisted bone end 9B2 and the bone shaft 9B3. the pins 61 and 62 are not inserted into the bone end 9B2 and the bone shaft 9B3, respectively, from the same direction, and the pins 61 and 62, as viewed from above the bone 9B, intersect each other on the bone axis. The axes A1, B1 and C1 of the external skeletal fixation device 1 in the state shown in FIG. 11, similarly to those in the state shown in FIG. 10, intersect each other at a virtual hinge point 9B1.

Referring to FIG. 12, the bone 9C connected to the external skeletal fixation device 1 is curved about a virtual hinge point 9C1. a bone end 9C2 and a bone shaft 9C3 on the opposite sides, respectively, of the virtual hinge point 9C1 are not twisted about the bone axis. In FIG. 12, the external skeletal fixation device 1 is attached to the curved bone 9C from the convex side of the bone 9C. The first bar link 41 and the second bar link 42 of the connecting mechanism 4, the first pin clamp unit 2 and the second pin clamp unit 3 are disposed in one and the same plane. The first pin clamp unit 2, the first bar link 41, the second bar link 42 and the second pin clamp unit 3 of the external skeletal fixation device 1 are arranged along a curve conforming to the curved bone 9C by turning the first bar link 41 and the second bar link 42 on the joints A, B and C to dispose the first pin clamp unit 2, the first bar link 41, the second bar link 42 and the second pin clamp unit 3 in one and the same plane.

When the external skeletal fixation device 1 is thus attached to the bone 9C, the axes A1, B1 and C1 intersect each other at the virtual hinge point 9C1. Thus the first pin-clamp unit 2 and the second pin clamp unit 3 can be disposed substantially parallel to the respective axes of the bone end 9C2 and the bone shaft 9C3, respectively, by turning the first bar link 41 and the second bar link 42 of the connecting mechanism 4 on the rotary joints A, B and C even if the respective axes of the bone end 9C2 and the bone shaft 9C3 are twisted. Thus the pins 61 and 62 held respectively by the first pin clamp unit 2 and the second pin clamp unit 3 can be properly inserted into the bone end 9C2 and the bone shaft 9C3 even if the bone end 9C2 and the bone shaft 9C3 are twisted.

Referring to FIG. 13, the bone 9D, similarly to the bone 9C shown in FIG. 12, connected to the external skeletal fixation device 1 is curved about a virtual hinge point 9D1. A bone end 9D2 and a bone shaft 9D3 on the opposite sides, respectively, of a virtual hinge point 9D1 are not twisted about the bone axis. In FIG. 13, the external skeletal fixation device 1 is attached to the curved bone 9C from the concave side of the bone 9D. The first bar link 41 and the second bar link 42 of the connecting mechanism 4 are extended so as to overlap each other to dispose the first pin clamp unit 2 and the second pin clamp unit 3 in one and the same plane.

The axes A1, B1 and C1 of turning of the external skeletal fixation device 1 as attachê to the bone 9D intersect each other at a virtual hinge point 9D1. Thus the first pin clamp unit 2 and the second pin clamp unit 3 can be disposed according to the degrees of twist of the bone axes of the bone end 9D2 and the bone shaft 9D3 and, consequently, the pins 61 and 62 can be inserted into the bone end 9D2 and the bone shaft 9D3, respectively.

The axes A1, B1 and C1 of turning of the external skeletal fixation device 1 intersect each other at the virtual hinge point on the bone to which the external skeletal fixation device 1 is attached. The first pin clamp unit 2 and the second pin clamp unit 3 can be properly disposed relative to the bone end and the bone shaft by turning the first bar link 41 and the second bar link 42 of the connecting mechanism 4 about the axes A1, B1 and C1.

(6) Deformity Correction of the Bone 9A

Deformity correction of the bone 9a by the external skeletal fixation device 1 will be described with reference to FIGS. 10 and 11.

(6-1) Correction of Rotational Deformity of the Bone 9B

Referring to FIG. 11, the respective axes of the bone end 9B2 and the bone shaft 9B3 of the bone 9B are twisted on the virtual hinge point 9B1. The virtual hinge point 9B1 is the center of deformation of the bone 9B. When osteotomy is applied to the deformity correction of the bone 9B, the bone end 9B2 and the bone shaft 9B3 respectively on the opposite sides of a dividing part are turned on the virtual hinge point 9B1. As mentioned above, the external skeletal fixation device 1 is attached to the bone 9B such that the pins 61 and 62 held by the external skeletal fixation device 1 are inserted into the bone end 9B2 and the bone shaft 9B3 substantially perpendicularly to the bone axes of the bone end 9B2 and the bone shaft 9B3, respectively. The worms 412B, 422B and 423B (FIGS. 5 and 6) of the rotary joints A, B and C are turned to turn the first bar link 41, the second pin clamp unit 3 and the second bar link 42 respectively in the directions of the arrows A2, B2 and C2 to move the second pin clamp unit 3 in the direction of the arrow S. After the second pin clamp unit 3 has been properly moved in the direction of the arrow S, an operation for turning the rotary joints A, B and C is stopped. The pins 61 held by the first pin clamp unit 2 are kept inserted into the bone end 9B2 and the pins 62 held by the second pin clamp unit 3 are kept inserted into the bond shaft 9B3 while the second pin clamp unit 3 is moved in the direction of the arrow S. Consequently, the bone shaft 9B3 is turned about its bone axis in the direction of the arrow S as the second pin clamp unit 3 is moved relative to the first pin clamp unit 2. The deformity correction operation for thus turning the bone shaft 9B3 is performed at a predetermined interval for a predetermined period so as to turn the bone shaft 9B3 through a predetermined angle at a time. Thus the rotational deformity of the bone 9B is corrected in a state similar to that of the bone 9A shown in FIG. 10.

The deformity correction operation for deformity correction of the twisted bone is applicable not only to the correction of substantially straight bones like the bone shown in FIG. 11, but also to the correction of other deformed bones, such as curved and rotated bones like those shown in FIGS. 12 and 13. The turning directions of the rotary joints A, B and C are not limited to the directions A2, B2 and C2 and may be turned in other directions, provided that the first pin clamp unit 2 and the second pin clamp unit 3 are moved relative to each other so that the rotated bone may be corrected.

(6-2) Lengthening of a Bone 9A

Figure 14:
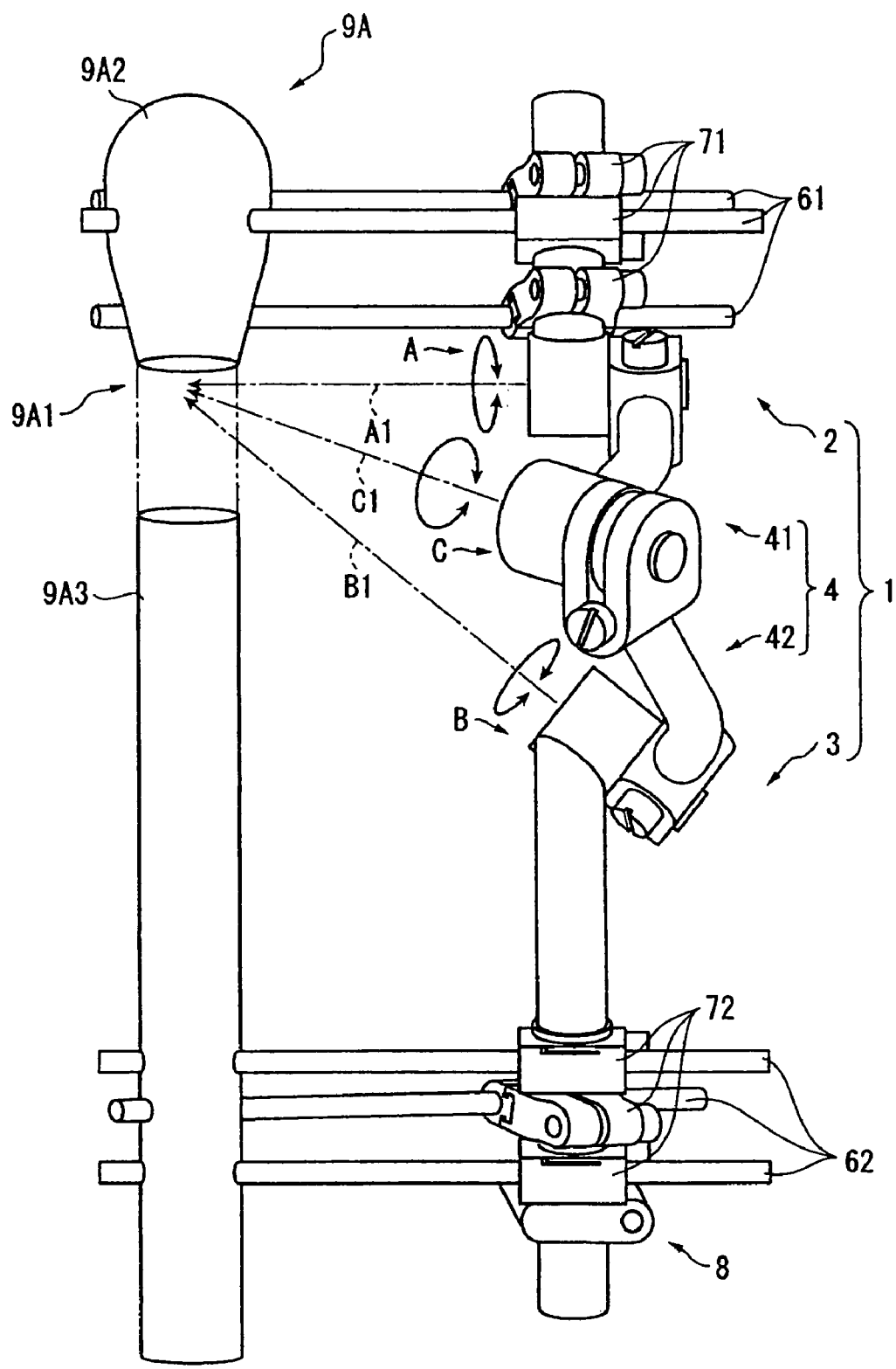
FIG. 14 is a perspective view of an lengthened bone.

FIG. 14 shows a bone 9A lengthened by using the external skeletal fixation device 1.

Referring to FIGS. 10 and 14, the lengthening of the bone 9A is achieved by a bone lengthening operation that moves the pin clamps 71 away from the pin clamps 72 or moves the pin clamps 72 away from the pin clamps 71. Referring to FIG. 10, the pin clamps 72 mounted on the diameter adjusting member 8 of the second pin clamp unit 3 are moved in the direction of the arrow T and are fixed at new positions to lengthen the bone 9A. Thus the bone lengthening operation increases the distance between the pin clamps 71 held by the first pin clamp unit 2 and the pin clamps 72 held by the second pin clamp unit 3. The bone lengthening operation is performed at a predetermined interval for a predetermined period until the distance between the bone end 9A2 and the bone shaft 9A3 is equal to a desired distance. When the bone end 9A2 and the bone shaft 9A3 are thus spaced apart, osteogenesis occurs in a region about the virtual hinge point 9A1 demarcated by two-dot chain lines in FIG. 14 and the lengthening of the bone 9A is achieved.

When all the pin clamps 72 of the second pin clamp unit 3 are mounted on the diameter adjusting member 8, pin clamps 72 can be moved simultaneously by moving the diameter adjusting member 8.

The bone lengthening operation is performed at the predetermined interval for the predetermined period to lengthen the bone by a desired length. The interval, the period and the incremental length may be selectively determined taking into consideration the conditions of the subject and the bone to be lengthened. For example, the bone lengthening operation is performed for some subjects for one to three months to lengthen the bone by a length in the range of about 0.5 to about 1.0 mm a day.

The deformity correction operation for correcting the torsional deformity of the bone and the bone lengthening operation may be performed simultaneously. Period, interval, angle and distance for correction may be simulated by a computer and data obtained by simulation may be used for planning actual bone deformity correction.

Effect of the First Embodiment

The external skeletal fixation device in the first embodiment has the following effects.

(7-1) The connecting mechanism 4 connects rodlike members 23 and 33 so that the first pin clamp unit 2 and the second pin clamp unit are turnable relative to each other. The first bar link 41 and the second bar link 42 of the connecting mechanism 4 are connected so as to be turnable relative to each other. The external skeletal fixation device 1 is a linkage including a pair of pin clamp units, namely, the first pin clamp unit 2 and the second pin clamp unit 3, a pair of arms, namely, the first bar link 41 and the second bar link 42, and the three rotary joints A, B and C connecting those elements of the linkage. The respective axes A1, B1 and C1 of the rotary joints A, B and C intersect each other at the respective virtual hinge points 91, 9A1, 9B1, 9C1 and 9D1 of the bones 9, 9A, 9B, 9C and 9D. Therefore, the external skeletal fixation device 1 can be three-dimensionally attached to the bone by turning the first bar link 41 and the second bar link 42 on the rotary joints A, B and C according to the shape of the bone. The external skeletal fixation device 1 can be properly attached to a bone of a complicated shape by optionally adjusting angles through which the components of the connecting mechanism 4 are turned on the rotary joints A, B and C. The decentering of the pins 61 and 62 inserted into the bone can be prevented and the undesired loading, such as twisting, of the external skeletal fixation device 1 and the bone can be prevented by turning the components of the connecting mechanism 4.

(7-2) The first bar link 41 and the second bar link 42 of the external skeletal fixation device 1 are allowed to turn on the rotary joints A, B and C and the first bar link 41 and the second bar link 42 are restrained from turning with bolts, not shown. Since the first pin clamp unit 2 and the second pin clamp unit 3 can be moved relative to each other by freely turning the first bar link 41 and the second bar link 42, the external skeletal fixation device 1 can be used for the deformity correction of the bone. Bone fragments can be turned and moved relative to each other about an objective part by the first pin clamp unit 2 and the second pin clamp unit 3 by turning the first bar link 41 and the second bar link 42 on the rotary joints A, B and C after attaching the external skeletal fixation device 1 to the bone fragments. Thus the amount of movement of the bone fragments and directions in which the bone fragments are moved can be freely determined. The bone can be corrected by repeating operations for turning, moving and fixing the bone fragments. The bone can be lengthened by axially moving the pin clamps 71 and 72 on the first pin clamp unit 2 and the second pin clamp unit 3. Thus, the degree of freedom of the amount of movement of bone fragments and the direction of corrective movement can be improved and, consequently, the bone can be freely corrected.

(7-3) The external skeletal fixation device 1 is a simple structure including the pair of pin clamp units, namely, the first pin clamp unit 2 and the second pin clamp unit 3 provided with the rodlike members 23 and 33, and the connecting mechanism 4 including the first bar link 41 and the second bar link 42. Thus, the external skeletal fixation device 1 is simple in construction.

(7-4) Since the external skeletal fixation device 1 is a monolateral external skeletal fixation device that inserts the pins 61 and 62 into a bone from one side of the bone, the external skeletal fixation device is simple in construction, the pair of pin clamp units can be three-dimensionally arrange so as to conform to the shape of the bone, the bone can be easily fixed and the external skeletal fixation device 1 is easy to handle. The external skeletal fixation device 1, as compared with the known external skeletal fixation device that is disposed so as to surround a fracture site and a part to be corrected of the bone, can be easily attached to the bone by an operator not having a special skill and experience. Since the external skeletal fixation device 1 is light and not bulky as compared with the known external skeletal fixation device, and the external skeletal fixation device 1 does not hinder the daily life of the patient who undergoes the surgical operation. Thus, the mental and physical loads on the patient of the external skeletal fixation device 1 can be effectively reduced.

(7-5) In the rotary joint A, the rotation of the worm 412B is transmitted through the worm wheel 412C engaged with the worm 412B to the small part 233B of the rodlike member 23 interlocked with the worm wheel 412C to turn the first pin clamp unit 2 and the first bar link 41 relative to each other. Thus, the angular position of the first bar link 41 relative to the first pin clamp unit 2 holding the pins 61 inserted into the bone end 92 can be adjusted by turning the worm 412B of the rotary joint A. Since the first bar link 41 can be turned on the rotary joint A by rotating the worm 412B after fixing the bone by the external skeletal fixation device 1, the deformed, twisted bone can be corrected and repositioned. The rotary joints B and C have the same effect as the rotary joint A.

(7-6) The rotary motion of the rotary joint A can be controlled by a bolt, not shown, that can engage with the worm wheel 412C. Thus, it is possible to prevent the accidental decentering of the pins 61 held by the external skeletal fixation device 1 due to the accidental turning of the first pin clamp unit 2 or the first bar link 41 on the rotary joint A by an unintentionally force applied to the external skeletal fixation device 1 during the operation for attaching the external skeletal fixation device 1 to the bone. Consequently, external skeletal fixation device 1 can be prevented from being damaged and the excessive loading of the patient's bone can be avoided. The rotary joints B and C similar in construction to the rotary joint A have the same effect.

(7-7) Since the middle part of each of the bar links is bent through about an angle of 40°, the external skeletal fixation device 1 can be fixed to the bone such that the respective axes A1, B1 and C1 of the rotary joints A, B and C intersect each other at the virtual hinge point. Therefore, the respective axes A1, B1 and C1 of the rotary joints A, B and C always intersect each other at the virtual hinge point even if the first bar link 41 and the second bar link 42 are turned. Consequently, the effect of making the axes A1, B1 and C1 intersect each other at the virtual hinge point is always effective.

(7-8) The component members of the external skeletal fixation device 1 are made of duralumin. Therefore, the external skeletal fixation device 1 is lightweight, and the external skeletal fixation device 1 attached to the bone and exposed outside the human body has a sufficient strength and is resistant to deformation. The lightweight external skeletal fixation device 1 can reduce load applied on the patient.

2. Second Embodiment

An external skeletal fixation device 1A in a second embodiment according to the present invention will be described. The external skeletal fixation device 1A in the second embodiment is substantially the same in construction as the external skeletal fixation device 1 in the first embodiment. The external skeletal fixation device 1A in the second embodiment has rotary joints A, B and C different in construction from those of the external skeletal fixation device 1. Parts of the external skeletal fixation device 1A like or corresponding to those of the external skeletal fixation device 1 are designated by the same reference characters and the description thereof will be omitted.

Figure 15:
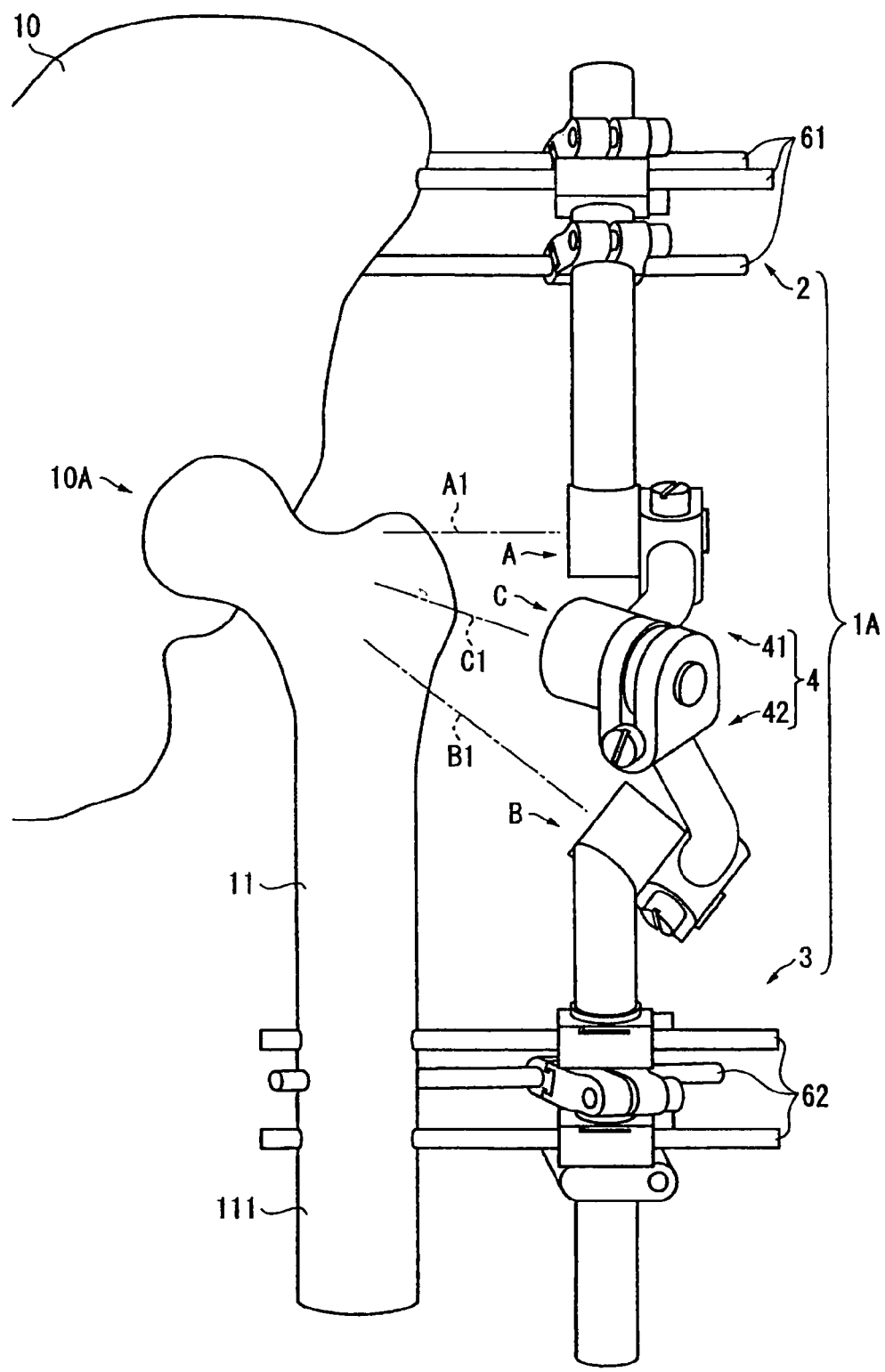
FIG. 15 is a perspective view of an external skeletal fixation device in a second embodiment according to the present invention.

FIG. 15 shows the external skeletal fixation device 1A in the second embodiment.

Referring to FIG. 15, the external skeletal fixation device 1A is attached to the pelvis 10 and the bone shaft 111 of the femur 11 so as to bridge over the hip joint 10A. The rotary joints A, B and C respectively having axes A1, B1 and C1 intersecting at a virtual hinge point of the external skeletal fixation device 1A are different from those of the external skeletal fixation device 1 in the first embodiment. Although not shown in FIG. 15, in the rotary joint A, a shaft part 233 of a rodlike member 23 included in a first pin clamp unit 2 is not interlocked by a key with a worm wheel 412C held by the connecting part 412 of a first bar link 41. Therefore, the first pin clamp unit 2 and the first bar link 41 are turned relative to each other on the rotary joint A without rotating the worm 412B. The rotary joints B and C are similar in construction to the rotary joint A; a second pin clamp unit 3 and a second bar link 42 are turned relative to each other on the rotary joint B and the first bar link 41 and the second bar link 42 are turned relative to each other on the rotary joint C without using the worms 423B and 422B.

Although the external skeletal fixation device 1A in the second embodiment as attached to the pelvis 10 and the bone shaft 111 of the femur 11 so as to bridge over the hip joint 10A is shown in FIG. 15 by way of example, the external skeletal fixation device 1A can be attached to bones so as to bridge over any one of joints such as a wrist joint, an elbow joint and a knee joint.

The external skeletal fixation device 1A in the second embodiment has the following effects in addition to effects similar to those mentioned in (7-1), (7-3), (7-4), (7-7) and (7-8).

The external skeletal fixation device 1A is constructed such that the first bar link 41 and the second bar link 42 thereof can be turned relative to each other on the rotary joints A, B and C without rotating the worms 412B, 423B and 422B, and the respective axes A1, B1 and C1 of the rotary joints A, B and C extend toward the virtual hinge point on the hip joint 10A. Partial or nonweight bearing of the hip joint 10A can be achieved and the load on the hip joint 10A can be reduced and disturbance to the motion of the hip joint 10A by the external skeletal fixation device 1A can be prevented by adjusting resistances of the rotary joints A, B and C against the turning of the first bar link 41 and the second bar link 42. In some cases, the known external skeletal fixation device not only disturbs the motions of the joint, but also strains the pins and the patient due to the decentering of the pins. The axes A1, B1 and C1 of the rotary joints A, B and C of the external skeletal fixation device 1A in the second embodiment extend toward the virtual hinge point on the femur 11, and the first bar link 41 and the second bar link 42 turn relative to each other on the rotary joints A, B and C so that the first pin clamp unit 2 and the second pin clamp unit 3 may move according to the movement of the pelvis 10 and the femur 11. Therefore, the decentering of the pins 61 and 62 inserted into the pelvis 10 and the femur 11 can be restricted, the bones can be securely fixed, and the motion of the joint joining the bones to which the external skeletal fixation device 1A is attached is not disturbed. Consequently, load on the joint can be reduced and walking exercise for rehabilitation for the patient with the external skeletal fixation device 1A can be started at an early stage after the operation.

3. Third Embodiment

Figure 16:
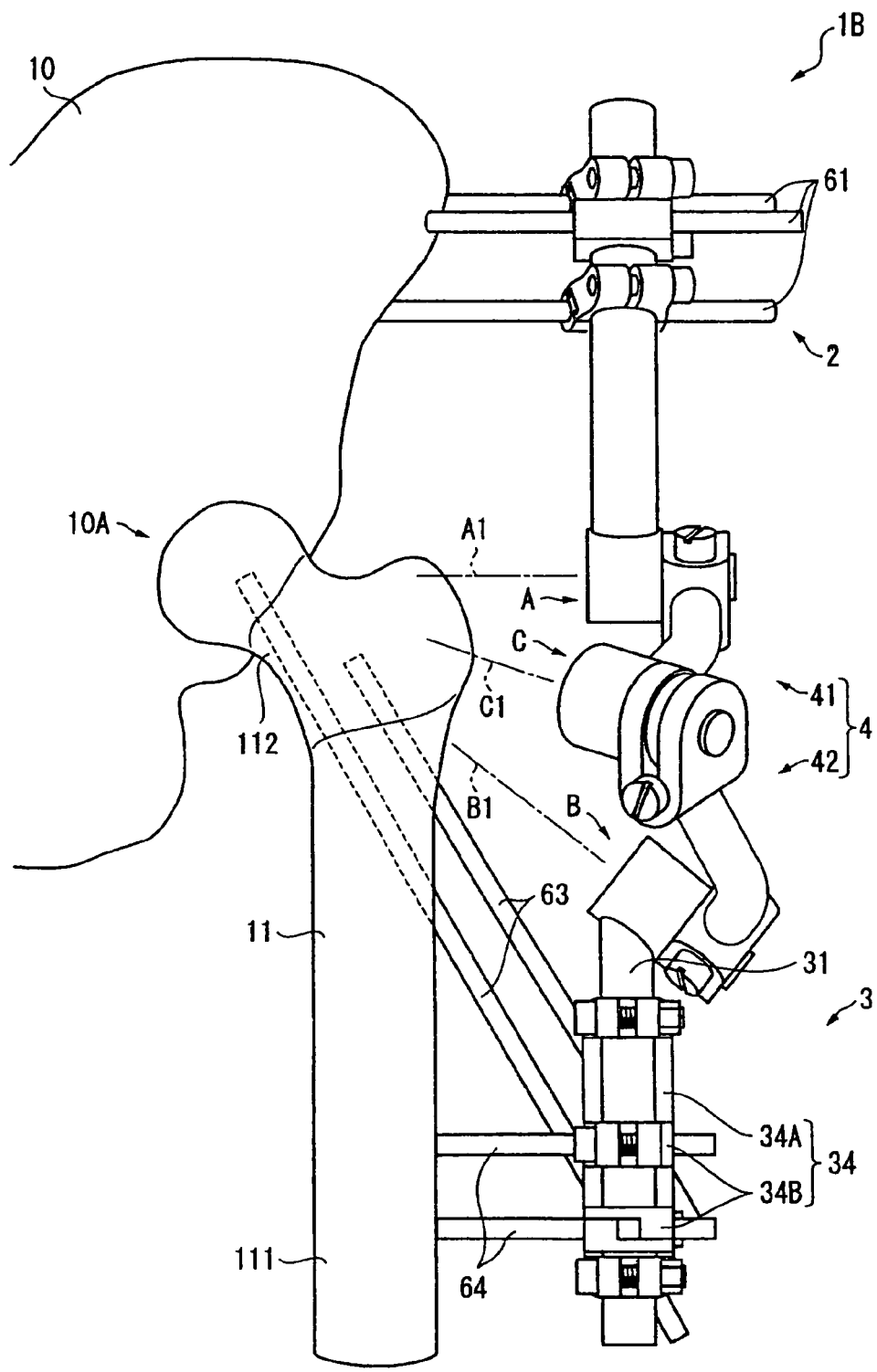
FIG. 16 is a perspective view of an external skeletal fixation device in a third embodiment according to the present invention.
Figure 17:
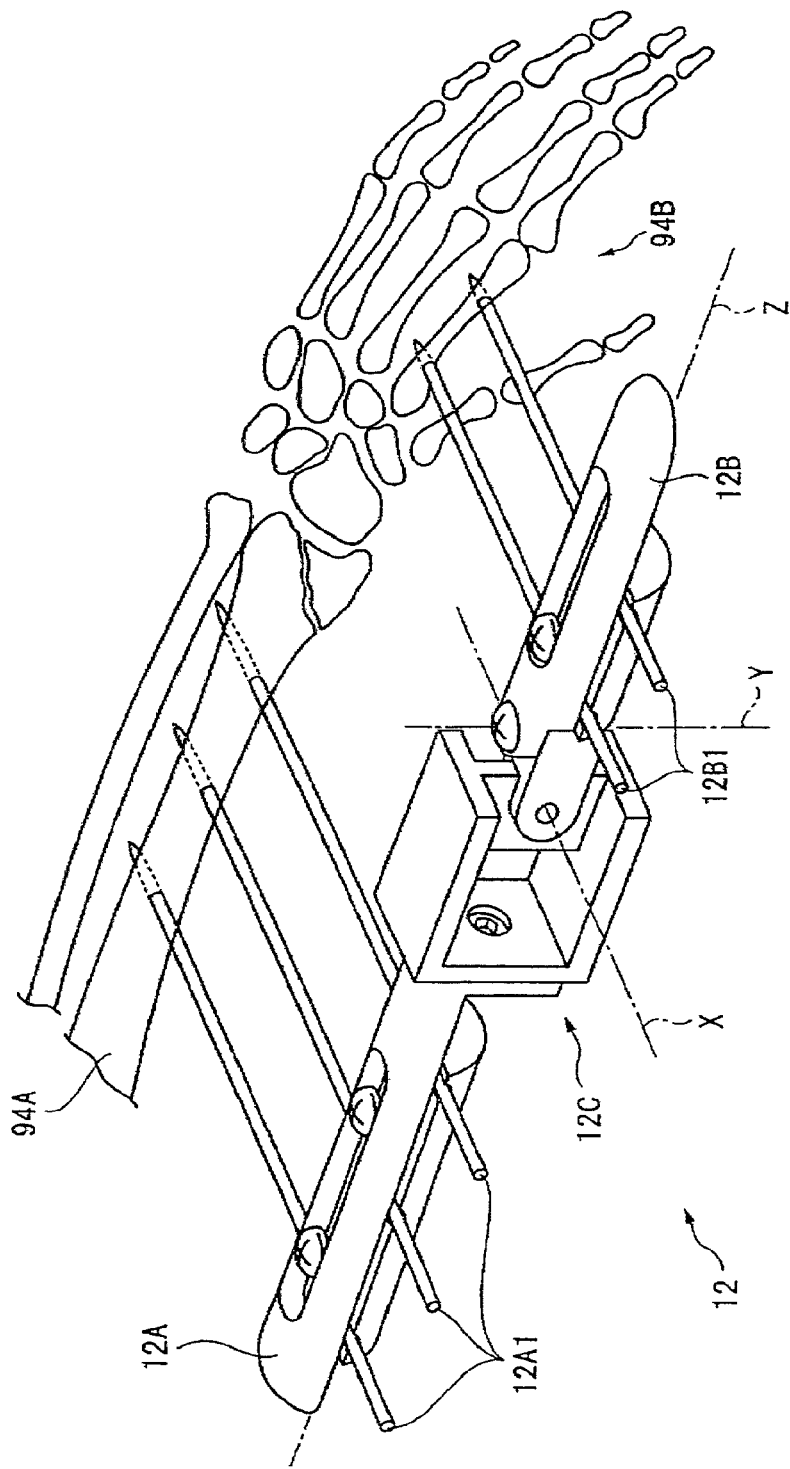
FIG. 17 is a perspective view of a known external skeletal fixation device.

FIG. 16 shows an external skeletal fixation device 1B in a third embodiment according to the present invention.

A second pin clamp unit 3 included in the external skeletal fixation device 1B in the third embodiment differs from those of the external skeletal fixation device 1 in the first embodiment and the external skeletal fixation device 1A in the second embodiment. Whereas the second pin clamp unit 3 of each of the external skeletal fixation devices 1 and 1A is provided with the pipe 31, the diameter adjusting member 8 put on the pipe 31 and the pin clamps 72 mounted on the diameter adjusting member 8, the second pin clamp unit 3 of the external skeletal fixation device 1B in the third embodiment is provided with a long bone fixing mechanism 34 for fixing a long bone. Pins 63 and 64 included in the long bone fixing mechanism 34 are inserted into the bone neck and the bone shaft, respectively, of the long bone.

Referring to FIG. 16, the external skeletal fixation device 1B includes a first pin clamp unit 2 holding pins 61 inserted into the pelvis 10, a second pin clamp unit 3 provided with the long bone fixing mechanism 34 holding the pins 63 and 64 inserted into the femoral neck 112 and the femoral shaft 111 of the femur 11, and a connecting mechanism 4 connecting the first pin clamp unit 2 and the second pin clamp unit 3. The respective axes A1, B1 and C1 of rotary joints A, B and C, on which a first bar link 41 and a second bar link 42 turn, extend toward a virtual hinge point, namely, the center of a fracture site or the center of the joint, on the femoral neck 112 or the hip joint 10A.

The pins 63 and 64 may be similar to either of the pins 61 and 62. The diameter and shape of the pins 63 and 64 may be changed when necessary.

The long bone fixing mechanism 34 includes a pin clamp member 34A attached to a pipe 31 included in the second pin clamp unit 3 and holding the pins 63, and pin clamp members 34B holding the pins 64 inserted into the femoral shaft 111.

The pin clamp member 34A has a sectional shape substantially resembling the letter C. The pipe 31 extends through a body part of the pin clamp member 34A. the two pins 63 are held on the outside surface of the pin clamp member 34A so as to extend at different angles, respectively, to the axis of the pipe 31. The pins 63 are inserted into the femoral neck 112 toward the bone axis in conformity with the angle between the femoral shaft 111 and the femoral neck 112.

The pin clamp members 34B holds the pins 64 inserted into the femoral shaft 111 so as to extend substantially perpendicularly to the bone axis of the femur 11. The pin clamp members 34B are similar in construction to, for example, the pin clamp members 72. A bolt fastens each of the pin clamp members 34B to achieve fastening the pin clamp member 34B to the pipe 31 and making the pin clamp member 34B grip the pin 64 simultaneously.

The external skeletal fixation device 1B in the third embodiment has the following effects in addition to effects similar to those mentioned in (7-1) to (7-8).

The external skeletal fixation device 1B in the third embodiment has the long bone fixing mechanism 34 for fixing the femur 11, namely, a long bone, mounted on the pipe 31 of the second pin clamp unit 3. The long bone fixing mechanism 34 is provided with the pin clamp member 34A holding the two pins 63 inserted into the femoral neck 112 at different angles, respectively, to the bone axis of the femoral neck 112 and pin clamp members 34B holding the two pins 64 inserted into the femoral shaft 111. The long bone fixing mechanism 34 can surely fix the femur 11 to achieve partial or nonweight bearing when the strength of the femur 11 is insufficient for walking due to the comminuted fracture of the femoral neck 112, due to the osteoporosis of the femur 11 or due to the discontinuous bone density of the femur 11. When the bar links of the external skeletal fixation device 1B, similarly to those of the external skeletal fixation device 1A in the second embodiment, are not turned on the rotary joints A, B and C by means of worms, the linkage of the connecting mechanism 4 does not disturb the motion of the hip joint 10A and hence walking exercise for rehabilitation for the patient with the external skeletal fixation device 1B can be started at an early stage after the operation and early walking exercise for rehabilitation enables the early return of the patient to society.

4. Modifications

The present invention is not limited in its practical application to the foregoing embodiments and changes and variations may be made therein. The following modifications are included in the present invention.

(4-1) The external skeletal fixation devices 1, 1A and 1B have been described as applied to fixing the bone after an operation, the external skeletal fixation devices 1, 1A and 1B may be used also as reduction devices during operations. When each of the external skeletal fixation devices 1, 1A and 1B is used as a reduction device, the pins 61 and 62 are inserted into the bone to be reduced and the first pin clamp unit 2 and the second pin clamp unit 3 are fixed. The external skeletal fixation devices 1, 1A or 1B is fixed such that the axes A1, B1 and C1 extend toward a virtual hinge point in a fracture site of the bone. Then, a manipulator is connected to the first bar link 41 and the second bar link 42 of the connecting mechanism 4, and the first bar link 41 and the second bar link 42 are turned by the manipulator to set the bone at a correct position. Thus the bone can be fixed during an operation and a treatment, such as postoperative walking exercise for rehabilitation, can be started with the bone thus fixed.

(4-2) The external skeletal fixation device 1 in the first embodiment has been described as attached to the single bone 9, and the external skeletal fixation devices 1A and 1B respectively in the second and the third embodiment have been described as attached to the pelvis 10 and the femur 11. The external skeletal fixation device of the present invention may be attached to other bones and may be attached to bones so as to bridge over other joint. For example, each of the external skeletal fixation devices 1, 1A and 1B may be attached to the humerus or the tibia and may be attached to bones so as to bridge over the shoulder joint, the wrist joint, the elbow joint or the knee joint.

(4-3) In the foregoing embodiments, the axis of the branch 332 of the rodlike member 33 of the second pin clamp unit 3 is inclined at about 40° to the axis of the shaft part 333, and the first bar link 41 and the second bar link 42 are bent through about 40°. Those angles are not limited to about 40°. The first bar link 41 and the second bar link 42 may be bent or straight and may be bent through an angle other than 40°, provided that the first bar link 41 and the second bar link 42 can turn relative to each other on the rotary joints A, B and C, and the axes A1, B1 and C1 of the rotary joints A, B and C extend toward the virtual hinge point. For example, in an external skeletal fixation device according to the present invention, rodlike members may be attached to end parts of a first and a second pin clamp unit, respectively at an angle not greater than 90°, and straight first and second bar links may be connected to the rodlike members, respectively.

(4-4) In each of the foregoing embodiments, the pipe 21 of the first pin clamp unit 2 is a hollow, cylindrical member of a length shorter than the pipe 31 of the second pin clamp unit 3.

The respective lengths and shapes of the pipes 21 and 31 are not limited thereto, and the shapes and the diameters of the pipes 21 and 31 may be properly determined so as to conform to the shape of a bone for which the external skeletal fixation device is designed.

(4-5) Although the pin holders 72 of the second pin clamp unit 3 are mounted on the diameter adjusting member 8 in the first and the second embodiment, the diameter adjusting member 8 may be omitted. The employment or omission of the diameter adjusting member 8 may be determined taking into consideration the shape of the pipe 31 and the diameter of the pins 62.

(4-6) Each of the pin clamps 71 for holding the pins 61 of the foregoing embodiments has the gripping member 711, the pin clamp member 712 and the fastening bolt 713 for fastening the gripping member 711 to the pipe 21 and fastening the pins 61 to the pin clamp member 712. The pins may be held by other pin holding mechanism. For example, a pin holding mechanism capable of gripping both the pipe 21 and the pins 61 may be employed. This applies also to the pin clamps 72, which is similar to the pin clamps 71.

(4-7) Although the diameter of the pins 61 is smaller than that of the pins 62 in the foregoing embodiments, the pins 61 and 62 may have any suitable shape and any suitable diameter. The pins 61 and 62 may have any shapes and any diameters, respectively, provided that the pins 61 and 62 can firmly fix bones to be fixed and can be held by the pin clamps 71 and 72 on the first pin clamp unit 2 and the second pin clamp unit 3, respectively. The pins 61 and 62 may be substantially the same pins.

(4-8) The component parts of the external skeletal fixation devices 1, 1A and 1B in the foregoing embodiments are supposed to be made of duralumin. Those component members may be made of a material other than duralumin. When the component members are made of titanium, the component members are corrosion-resistant and are stable for a long time. Although the pins 61 and 62 are supposed to be made of metal, such as a stainless steel or titanium in the foregoing description, the pins 61 and 62 may be made of other material.

The invention claimed is:

1. An external skeletal fixation device comprising:
a first pin clamp unit for fixedly holding rodlike members adapted to be inserted into a first part of a bone;
a second pin clamp unit for fixedly holding rodlike members adapted to be inserted into a second part of a bone on an opposite side, respectively, of a virtual hinge point corresponding to a center of rotational angulation of the bone, a center on which the first and the second part of the bone respectively on the opposite sides of a fracture site of the bone or an osteotomy site for correction are turned, or a center about which a joint turns;
a first arm having a proximal end and a distal end, said distal end being operatively connected to said first pin clamp unit;
a second arm having a proximal end and a distal end, said distal end being operatively connected to the second pin clamp unit; and
a connecting mechanism connecting the proximal end of the first arm to the proximal end of the second arm;
a first shaft operatively connected to either said first pin clamp unit or said distal end of the first arm to turnably connect the first pin clamp unit relative to the first arm, said first shaft having an axis projecting in a direction to extend toward and substantially intersect at the virtual hinge point;
a second shaft operatively connected to either the second pin clamp unit or said distal end of the second arm to turnably connect the second pin clamp unit relative to the second arm, said second shaft having an axis projecting in a direction to extend toward and substantially intersect at the virtual hinge point;
a connecting shaft being operatively connected to either said proximal end of said first arm or said proximal end of said second arm for pivotally joining the first and second arms together, said connecting shaft including an axis projecting in a direction to extend toward and substantially intersect at the virtual hinge point;
wherein an extension from said axis of the first shaft, an extension from the axis of the second shaft and an extension from the axis of the connecting shaft extend towards and substantially intersect at said virtual hinge point; and wherein the first shaft, the second shaft and the connecting shaft include ring parts formed on an end of the first shaft, the second shaft and the connecting shaft and retaining rings positioned on the ends of the first shaft, the second shaft and the connecting shaft to press the ring parts against base parts of the first shaft, the second shaft and the connecting shaft, respectively, worm wheels attached to the first shaft, the second shaft and the connecting shaft and provided with teeth arranged around the circumferences thereof, respectively, and worms supported on end parts of the ring parts so as to extend parallel to tangents to the inner circumferences of the ring parts and engaged with the worm wheels, respectively.

2. The external skeletal fixation device according to claim 1, wherein each of the first and the second arms has a middle part bent through an angle of approximately 40°.

3. The external skeletal fixation device according to claim 1, wherein the deviceis made of metal.

4. The external skeletal fixation device according to claim 1, wherein said first pin clamp unit includes the first shaft coupled to a base part, a pipe extending from said base part and pin clamps adjustably secured to the pipe for positioning the rodlike members adapted to be inserted into a first part of a bone.

5. The external skeletal fixation device according to claim 1, wherein said second pin clamp unit includes the second shaft coupled to a base part, a pipe extending from said base part and pin clamps adjustably secured to the pipe for positioning the rodlike members adapted to be inserted into a first part of a bone.

6. The external skeletal fixation device according to claim 1, wherein said first arm is substantially L-shaped.

7. The external skeletal fixation device according to claim 1, wherein said second arm is substantially S-shaped.

8. An external skeletal fixation device comprising:
a first pin clamp unit for fixedly holding rodlike members adapted to be inserted into a first part of a bone;
a second pin clamp unit for fixedly holding rodlike members adapted to be inserted into a second part of a bone on an opposite side, respectively, of a virtual hinge point corresponding to a center of rotational angulation of the bone, a center on which the first and the second part of the bone respectively on the opposite sides of a fracture site of the bone or an osteotomy site for correction are turned, or a center about which a joint turns;
a first arm having a proximal end and a distal end, said distal end being operatively connected to said first pin clamp unit;
a second arm having a proximal end and a distal end, said distal end being operatively connected to the second pin clamp unit; and a connecting mechanism connecting the proximal end of the first arm to the proximal end of the second arm;

a first shaft operatively connected to either said first pin clamp unit or said distal end of the first arm to turnably connect the first pin clamp unit relative to the first arm, said first pin clamp shaft having an axis projecting in a direction to extend toward and substantially intersect at the virtual hinge point;

a connecting shaft being operatively connected to either said proximal end of said first arm or said proximal end of said second arm for pivotally joining the first and second arms together, said connecting shaft including an axis projecting in a direction to extend toward and substantially intersect at the virtual hinge point;

wherein an extension from said axis of the first shaft and an extension from the axis of the connecting shaft extend towards and substantially intersect at said virtual hinge point; and wherein the first shaft and the connecting shaft include: ring parts formed on an end of the first shaft and the connecting shaft and retaining rings positioned on the ends of the first shaft and the connecting shaft to press the ring parts against base parts of the first shaft and the connecting shaft, respectively, worm wheels attached to the first shaft and the connecting shaft and provided with teeth arranged around the circumferences thereof, respectively, and worms supported on end parts of the ring parts so as to extend parallel to tangents to the inner circumferences of the ring parts and engaged with the worm wheels, respectively.

9. The external skeletal fixation device according to claim 8, wherein each of the first and the second arms has a middle part bent through an angle of approximately 40°.

10. The external skeletal fixation device according to claim 8, wherein the device is made of metal.

11. The external skeletal fixation device according to claim 8, wherein said first pin clamp unit includes the first shaft coupled to a base part, a pipe extending from said base part and pin clamps adjustably secured to the pipe for positioning the rodlike members adapted to be inserted into a first part of a bone.

12. The external skeletal fixation device according to claim 8, wherein said second pin clamp unit includes a second shaft coupled to a base part, a pipe extending from said base part and pin clamps adjustably secured to the pipe for positioning the rodlike members adapted to be inserted into a first part of a bone.

13. The external skeletal fixation device according to claim 8, wherein said first arm is substantially L-shaped.

14. The external skeletal fixation device according to claim 8, wherein said second arm is substantially S-shaped.

* * * * *